United States Patent
Montello et al.

(10) Patent No.: US 12,089,877 B2
(45) Date of Patent: Sep. 17, 2024

(54) REVISION CONNECTOR FOR SPINAL CONSTRUCTS

(71) Applicant: DePuy Synthes Products, Inc., Raynham, MA (US)

(72) Inventors: Albert Montello, Duxbury, MA (US); Oleg Levin, Chester Springs, PA (US); William Strausbaugh, Myerstown, PA (US); Thomas Kueenzi, Magden (CH)

(73) Assignee: DePuy Synthes Products, Inc., Raynham, MA (US)

( * ) Notice: Subject to any disclaimer, the term of this patent is extended or adjusted under 35 U.S.C. 154(b) by 276 days.

(21) Appl. No.: 17/231,256

(22) Filed: Apr. 15, 2021

(65) Prior Publication Data
US 2021/0244448 A1     Aug. 12, 2021

Related U.S. Application Data

(63) Continuation of application No. 15/349,509, filed on Nov. 11, 2016, now Pat. No. 11,006,978, which is a
(Continued)

(51) Int. Cl.
*A61B 17/70*     (2006.01)

(52) U.S. Cl.
CPC ...... *A61B 17/7025* (2013.01); *A61B 17/7001* (2013.01); *A61B 17/7002* (2013.01);
(Continued)

(58) Field of Classification Search
CPC ............ A61B 17/7011; A61B 17/7032; A61B 17/7034; A61B 17/7035; A61B 17/7041;
(Continued)

(56) References Cited

U.S. PATENT DOCUMENTS

| 405,546 A | 6/1889 | Frist |
|---|---|---|
| 513,630 A | 1/1894 | Beard |

(Continued)

FOREIGN PATENT DOCUMENTS

| CA | 2289629 A1 | 11/1998 |
|---|---|---|
| CN | 102368967 A | 3/2012 |

(Continued)

OTHER PUBLICATIONS

"Secure" Cambridge Dictionary accessed Feb. 27, 2021 https://dictionary.cambridge.org/us/dictionary/english/secure (Year: 2021).
(Continued)

*Primary Examiner* — Nicholas J Plionis
*Assistant Examiner* — Christina Negrellirodriguez
(74) *Attorney, Agent, or Firm* — BakerHostetler

(57) ABSTRACT

An extender system is configured to couple a vertebral bone anchor that has been previously implanted in a vertebra, or is newly implantable in a vertebra, to an adjacent bone, which can be an additional spinal level or an occiput, for example. The extender system includes an extension member having a body and an engagement member coupled to the body. The extension member defines an aperture extending through the engagement member. A screw is configured to attach the extension member to the vertebral bone anchor. The extension member can be fastened to the adjacent bone.

20 Claims, 20 Drawing Sheets

Related U.S. Application Data continuation of application No. 12/817,920, filed on Jun. 17, 2010, now Pat. No. 9,510,862.

(60) Provisional application No. 61/187,902, filed on Jun. 17, 2009.

(52) U.S. Cl.
 CPC ...... *A61B 17/7007* (2013.01); *A61B 17/7011* (2013.01); *A61B 17/7032* (2013.01); *A61B 17/7049* (2013.01)

(58) Field of Classification Search
 CPC .............. A61B 17/7025; A61B 17/702; Y10T 403/32204; Y10T 403/32737
 USPC .................................................. 606/256–257
 See application file for complete search history.

(56) References Cited

U.S. PATENT DOCUMENTS

| | | |
|---|---|---|
| 802,896 A | 10/1905 | Webb |
| 2,005,348 A | 6/1935 | Anthony |
| 2,338,659 A | 1/1944 | Morehouse |
| 2,396,925 A | 3/1946 | Morehouse |
| 3,173,987 A | 3/1965 | Potruch |
| 3,463,427 A | 8/1969 | Fisher |
| 4,447,934 A | 5/1984 | Anscher |
| 4,601,491 A | 7/1986 | Bell et al. |
| 4,719,905 A | 1/1988 | Steffee |
| 4,805,602 A | 2/1989 | Puno et al. |
| 4,846,614 A | 7/1989 | Steinbock |
| 4,863,383 A | 9/1989 | Grafelmann |
| 4,936,851 A | 6/1990 | Fox et al. |
| 4,944,475 A | 7/1990 | Ono et al. |
| 4,946,458 A | 8/1990 | Harms et al. |
| 5,005,562 A | 4/1991 | Cotrel |
| 5,116,337 A | 5/1992 | Johnson |
| 5,129,388 A | 7/1992 | Vignaud et al. |
| 5,207,678 A | 5/1993 | Harms et al. |
| 5,242,446 A | 9/1993 | Steffee et al. |
| 5,270,678 A | 12/1993 | Gambut et al. |
| 5,282,825 A | 2/1994 | Muck et al. |
| 5,304,178 A | 4/1994 | Stahurski |
| 5,306,275 A | 4/1994 | Bryan |
| 5,306,285 A | 4/1994 | Miller et al. |
| 5,312,410 A | 5/1994 | Miller et al. |
| 5,360,431 A | 11/1994 | Puno et al. |
| 5,383,882 A | 1/1995 | Buess et al. |
| 5,395,374 A | 3/1995 | Miller et al. |
| 5,413,576 A | 5/1995 | Rivard |
| 5,413,602 A | 5/1995 | Metz-Stavenhagen |
| 5,417,684 A | 5/1995 | Jackson et al. |
| 5,443,467 A | 8/1995 | Biedermann et al. |
| 5,449,361 A | 9/1995 | Preissman |
| 5,466,237 A | 11/1995 | Byrd et al. |
| 5,468,241 A | 11/1995 | Metz-Stavenhagen et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,496,321 A | 3/1996 | Puno et al. |
| 5,498,262 A | 3/1996 | Bryan |
| 5,501,684 A | 3/1996 | Schlapfer et al. |
| 5,520,689 A | 5/1996 | Schlapfer et al. |
| 5,520,690 A | 5/1996 | Errico et al. |
| 5,527,183 A | 6/1996 | O'Brien |
| 5,531,746 A | 7/1996 | Errico et al. |
| 5,534,001 A | 7/1996 | Schlapfer et al. |
| 5,536,268 A | 7/1996 | Griss |
| 5,536,270 A | 7/1996 | Songer et al. |
| 5,540,698 A | 7/1996 | Preissman |
| 5,549,608 A | 8/1996 | Errico et al. |
| 5,549,677 A | 8/1996 | Duerr et al. |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,832 A | 12/1996 | Schlaepfer |
| 5,584,834 A | 12/1996 | Errico et al. |
| 5,586,984 A | 12/1996 | Errico et al. |
| 5,601,261 A | 2/1997 | Koike |
| 5,601,429 A | 2/1997 | Blacklock |
| 5,605,457 A | 2/1997 | Bailey et al. |
| 5,605,458 A | 2/1997 | Bailey et al. |
| 5,607,304 A | 3/1997 | Bailey et al. |
| 5,607,426 A | 3/1997 | Ralph et al. |
| 5,609,593 A | 3/1997 | Errico et al. |
| 5,609,594 A | 3/1997 | Errico et al. |
| 5,624,442 A | 4/1997 | Mellinger et al. |
| 5,643,260 A | 7/1997 | Doherty |
| 5,643,262 A | 7/1997 | Metz-Stavenhagen et al. |
| 5,643,265 A | 7/1997 | Errico et al. |
| 5,645,544 A | 7/1997 | Tai et al. |
| 5,647,873 A | 7/1997 | Errico et al. |
| 5,662,651 A | 9/1997 | Tornier et al. |
| 5,667,508 A | 9/1997 | Errico et al. |
| 5,669,911 A | 9/1997 | Errico et al. |
| 5,672,175 A | 9/1997 | Martin |
| 5,683,390 A | 11/1997 | Metz-Stavenhagen et al. |
| 5,683,392 A | 11/1997 | Richelsoph et al. |
| 5,683,404 A | 11/1997 | Johnson |
| 5,688,273 A | 11/1997 | Errico et al. |
| 5,690,630 A | 11/1997 | Errico et al. |
| 5,694,760 A | 12/1997 | Baxter |
| 5,704,939 A | 1/1998 | Justin |
| 5,725,582 A | 3/1998 | Bevan et al. |
| 5,725,588 A | 3/1998 | Errico et al. |
| 5,728,098 A | 3/1998 | Sherman et al. |
| 5,733,285 A | 3/1998 | Errico et al. |
| 5,738,685 A | 4/1998 | Halm et al. |
| 5,772,663 A | 6/1998 | Whiteside et al. |
| 5,782,831 A | 7/1998 | Sherman et al. |
| 5,782,833 A | 7/1998 | Haider |
| 5,797,911 A | 8/1998 | Sherman et al. |
| 5,810,818 A | 9/1998 | Errico et al. |
| 5,817,094 A | 10/1998 | Errico et al. |
| 5,860,987 A | 1/1999 | Ratcliff et al. |
| 5,863,293 A | 1/1999 | Richelsoph |
| 5,868,748 A | 2/1999 | Burke |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,899,940 A | 5/1999 | Carchidi et al. |
| 5,902,305 A | 5/1999 | Beger et al. |
| 5,938,663 A | 8/1999 | Petreto |
| 5,951,287 A | 9/1999 | Hawkinson |
| 5,961,329 A | 10/1999 | Stucki-McCormick |
| 5,964,760 A | 10/1999 | Richelsoph |
| 6,001,098 A | 12/1999 | Metz-Stavenhagen et al. |
| 6,010,503 A | 1/2000 | Richelsoph et al. |
| 6,015,409 A | 1/2000 | Jackson |
| 6,017,177 A | 1/2000 | Lanham |
| 6,019,760 A | 2/2000 | Metz-Stavenhagen et al. |
| 6,022,350 A | 2/2000 | Ganem |
| 6,053,917 A | 4/2000 | Sherman et al. |
| 6,063,090 A | 5/2000 | Fridolin |
| 6,074,391 A | 6/2000 | Metz-Stavenhagen et al. |
| 6,077,262 A | 6/2000 | Schlaepfer et al. |
| 6,077,263 A | 6/2000 | Ameil et al. |
| 6,083,224 A | 7/2000 | Gertzbein et al. |
| 6,090,110 A | 7/2000 | Metz-Stavenhagen |
| 6,126,662 A | 10/2000 | Carmichael et al. |
| 6,132,432 A | 10/2000 | Richelsoph |
| 6,183,472 B1 | 2/2001 | Lutz |
| 6,214,006 B1 | 4/2001 | Metz-Stavenhagen |
| 6,217,331 B1 | 4/2001 | Rogers et al. |
| 6,224,598 B1 | 5/2001 | Jackson |
| 6,248,105 B1 | 6/2001 | Schlaepfer et al. |
| 6,261,287 B1 | 7/2001 | Metz-Stavenhagen |
| 6,273,914 B1 | 8/2001 | Papas |
| 6,280,442 B1 | 8/2001 | Barker et al. |

(56) References Cited

U.S. PATENT DOCUMENTS

| | | |
|---|---|---|
| 6,296,642 B1 | 10/2001 | Morrison et al. |
| 6,325,802 B1 | 12/2001 | Frigg |
| 6,355,040 B1 | 3/2002 | Richelsoph et al. |
| 6,361,535 B2 | 3/2002 | Jackson |
| RE37,665 E | 4/2002 | Ralph et al. |
| 6,368,320 B1 | 4/2002 | Le Couedic et al. |
| 6,368,321 B1 | 4/2002 | Jackson |
| 6,402,752 B2 | 6/2002 | Schaeffler-Wachter et al. |
| 6,440,132 B1 | 8/2002 | Jackson |
| 6,443,953 B1 | 9/2002 | Perra et al. |
| 6,443,955 B1 | 9/2002 | Ahrend et al. |
| 6,451,021 B1 | 9/2002 | Ralph et al. |
| 6,454,768 B1 | 9/2002 | Jackson |
| 6,454,772 B1 | 9/2002 | Jackson |
| 6,471,705 B1 | 10/2002 | Biedermann et al. |
| 6,482,207 B1 | 11/2002 | Errico |
| 6,485,491 B1 | 11/2002 | Farris et al. |
| 6,491,696 B1 | 12/2002 | Kunkel |
| 6,508,820 B2 | 1/2003 | Bales |
| 6,514,255 B1 | 2/2003 | Ferree |
| 6,520,963 B1 | 2/2003 | McKinley |
| 6,533,226 B2 | 3/2003 | Geiger |
| 6,537,070 B1 | 3/2003 | Stucki-McCormick |
| 6,537,276 B2 | 3/2003 | Metz-Stavenhagen |
| 6,554,831 B1 | 4/2003 | Rivard et al. |
| 6,558,387 B2 | 5/2003 | Errico et al. |
| 6,565,565 B1 | 5/2003 | Yuan et al. |
| 6,585,740 B2 | 7/2003 | Schlapfer et al. |
| 6,616,667 B1 | 9/2003 | Steiger et al. |
| 6,626,908 B2 | 9/2003 | Cooper et al. |
| 6,641,586 B2 | 11/2003 | Varieur |
| 6,641,588 B2 | 11/2003 | Citron et al. |
| 6,660,004 B2 | 12/2003 | Barker et al. |
| 6,689,140 B2 | 2/2004 | Cohen |
| 6,695,852 B2 | 2/2004 | Gleason |
| 6,716,214 B1 | 4/2004 | Jackson |
| 6,726,687 B2 | 4/2004 | Jackson |
| 6,736,820 B2 | 5/2004 | Biedermann et al. |
| 6,738,527 B2 | 5/2004 | Kuwata et al. |
| 6,740,086 B2 | 5/2004 | Richelsoph |
| 6,749,613 B1 | 6/2004 | Conchy et al. |
| 6,755,829 B1 | 6/2004 | Bono et al. |
| 6,770,075 B2 | 8/2004 | Howland |
| 6,780,186 B2 | 8/2004 | Errico et al. |
| 6,783,527 B2 | 8/2004 | Drewry et al. |
| 6,802,844 B2 | 10/2004 | Ferree |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,866,664 B2 | 3/2005 | Schaer et al. |
| 6,869,433 B2 | 3/2005 | Glascott |
| 6,887,275 B2 | 5/2005 | Carchidi et al. |
| 6,918,911 B2 | 7/2005 | Biedermann et al. |
| 6,933,440 B2 | 8/2005 | Ichikawa et al. |
| 6,964,666 B2 | 11/2005 | Jackson |
| 6,974,460 B2 | 12/2005 | Carbone et al. |
| 6,981,973 B2 | 1/2006 | McKinley |
| 7,008,227 B2 | 3/2006 | Carmichael et al. |
| 7,018,378 B2 | 3/2006 | Biedermann et al. |
| RE39,089 E | 5/2006 | Ralph et al. |
| 7,073,415 B2 | 7/2006 | Casutt et al. |
| 7,081,117 B2 | 7/2006 | Bono et al. |
| 7,087,057 B2 | 8/2006 | Konieczynski et al. |
| 7,094,240 B2 * | 8/2006 | Molz, IV ............... A61B 17/88 606/103 |
| D527,678 S | 9/2006 | Warner |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,131,467 B2 | 11/2006 | Gao et al. |
| 7,144,396 B2 | 12/2006 | Shluzas |
| 7,163,539 B2 | 1/2007 | Abdelgany et al. |
| 7,175,622 B2 | 2/2007 | Farris |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,270,665 B2 | 9/2007 | Morrison et al. |
| 7,316,684 B1 | 1/2008 | Baccelli et al. |
| 7,322,548 B2 | 1/2008 | Mielke et al. |
| 7,330,490 B2 | 2/2008 | Furukawa et al. |
| 7,338,490 B2 | 3/2008 | Ogilvie et al. |
| 7,445,627 B2 | 11/2008 | Hawkes et al. |
| 7,452,360 B2 | 11/2008 | Trudeau et al. |
| 7,476,239 B2 | 1/2009 | Jackson |
| 7,547,319 B2 | 6/2009 | Segal et al. |
| 7,572,281 B2 | 8/2009 | Runco et al. |
| 7,591,839 B2 | 9/2009 | Biedermann et al. |
| 7,592,546 B2 | 9/2009 | Johansson |
| 7,645,282 B2 | 1/2010 | Huxel et al. |
| 7,648,520 B2 | 1/2010 | Markworth |
| 7,691,131 B2 | 4/2010 | Graf |
| 7,708,762 B2 | 5/2010 | McCarthy et al. |
| 7,766,944 B2 | 8/2010 | Metz-Stavenhagen |
| 7,780,706 B2 | 8/2010 | Marino et al. |
| 7,785,352 B2 | 8/2010 | Snyder et al. |
| 7,785,354 B2 | 8/2010 | Biedermann et al. |
| 7,799,054 B2 | 9/2010 | Kwak et al. |
| 7,803,174 B2 | 9/2010 | Denis et al. |
| 7,806,895 B2 | 10/2010 | Weier et al. |
| 7,819,902 B2 | 10/2010 | Abdelgany et al. |
| 7,951,172 B2 | 5/2011 | Chao et al. |
| 7,967,849 B2 | 6/2011 | Carson et al. |
| 8,001,946 B2 | 8/2011 | Leitl |
| 8,002,806 B2 | 8/2011 | Justis |
| 8,029,513 B2 | 10/2011 | Konno et al. |
| 8,029,544 B2 * | 10/2011 | Hestad ............... A61B 17/7031 606/255 |
| 8,029,546 B2 | 10/2011 | Capote et al. |
| 8,038,701 B2 | 10/2011 | Rock et al. |
| 8,096,998 B2 | 1/2012 | Cresina |
| 8,100,946 B2 | 1/2012 | Strausbaugh et al. |
| 8,137,356 B2 | 3/2012 | Hestad et al. |
| 8,162,946 B2 | 4/2012 | Baccelli et al. |
| 8,162,986 B2 | 4/2012 | Zehnder |
| 8,172,772 B2 | 5/2012 | Zwolinski et al. |
| 8,197,517 B1 | 6/2012 | Lab et al. |
| 8,216,245 B2 | 7/2012 | Gil et al. |
| 8,221,464 B2 | 7/2012 | Belliard et al. |
| 8,231,626 B2 | 7/2012 | Hulliger et al. |
| 8,241,333 B2 | 8/2012 | Jackson |
| 8,246,659 B2 | 8/2012 | Vonwiller et al. |
| 8,257,367 B2 | 9/2012 | Bryant et al. |
| 8,308,782 B2 | 11/2012 | Jackson |
| 8,317,836 B2 | 11/2012 | Zucherman et al. |
| 8,323,318 B2 | 12/2012 | Baccelli et al. |
| 8,444,681 B2 | 5/2013 | Jackson et al. |
| 8,469,960 B2 | 6/2013 | Hutton et al. |
| 8,469,966 B2 | 6/2013 | Allen et al. |
| 8,556,938 B2 | 10/2013 | Jackson et al. |
| 8,628,558 B2 | 1/2014 | Harvey et al. |
| 8,632,572 B2 | 1/2014 | Darst et al. |
| 8,663,298 B2 | 3/2014 | Keyer et al. |
| 8,758,411 B1 | 6/2014 | Rayon et al. |
| 8,814,910 B2 | 8/2014 | Baccelli et al. |
| 8,840,652 B2 | 9/2014 | Jackson |
| 8,870,869 B2 | 10/2014 | Meunier et al. |
| 8,870,870 B2 | 10/2014 | Baccelli et al. |
| 8,882,803 B2 | 11/2014 | Iott et al. |
| 8,911,470 B2 | 12/2014 | Mirza et al. |
| 8,911,478 B2 | 12/2014 | Jackson et al. |
| 8,911,479 B2 | 12/2014 | Jackson et al. |
| 8,926,672 B2 | 1/2015 | Jackson et al. |
| 8,979,904 B2 | 3/2015 | Jackson et al. |
| 8,998,959 B2 | 4/2015 | Jackson et al. |
| 8,998,961 B1 | 4/2015 | Ziemek et al. |
| 9,039,708 B2 | 5/2015 | Larroque-Lahitette |
| 9,168,069 B2 | 10/2015 | Jackson et al. |
| 9,216,041 B2 | 12/2015 | Jackson et al. |
| 9,320,546 B2 | 4/2016 | Keyer et al. |
| 9,326,796 B2 | 5/2016 | Harvey et al. |
| 9,393,047 B2 | 7/2016 | Jackson et al. |
| 9,439,681 B2 | 9/2016 | Keyer et al. |

(56) References Cited

U.S. PATENT DOCUMENTS

| | | |
|---|---|---|
| 9,451,993 B2 | 9/2016 | Jackson et al. |
| 9,480,517 B2 | 11/2016 | Jackson et al. |
| 9,504,496 B2 | 11/2016 | Jackson et al. |
| 9,522,021 B2 | 12/2016 | Jackson et al. |
| 9,636,146 B2 | 5/2017 | Jackson et al. |
| 9,717,533 B2 | 8/2017 | Jackson et al. |
| 9,717,534 B2 | 8/2017 | Jackson et al. |
| 10,105,163 B2 | 10/2018 | Keyer et al. |
| 10,136,923 B2 | 11/2018 | Keyer et al. |
| 10,154,859 B2 | 12/2018 | Keyer et al. |
| 10,405,892 B2 | 9/2019 | Harvey et al. |
| 10,595,908 B2 | 3/2020 | Strausbaugh et al. |
| 11,357,550 B2 | 6/2022 | Keyer et al. |
| 2001/0047173 A1 | 11/2001 | Schlapfer et al. |
| 2002/0045899 A1 | 4/2002 | Errico et al. |
| 2002/0068940 A1 | 6/2002 | Gaines |
| 2002/0069537 A1 | 6/2002 | Wenzler |
| 2002/0072753 A1 | 6/2002 | Cohen |
| 2002/0103487 A1 | 8/2002 | Errico et al. |
| 2002/0117321 A1 | 8/2002 | Beebe et al. |
| 2002/0120272 A1 | 8/2002 | Yuan et al. |
| 2002/0133154 A1* | 9/2002 | Saint Martin ...... A61B 17/7037 606/264 |
| 2002/0138077 A1 | 9/2002 | Ferree |
| 2002/0143341 A1 | 10/2002 | Biedermann et al. |
| 2002/0151900 A1 | 10/2002 | Glascott |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0125742 A1 | 7/2003 | Yuan et al. |
| 2003/0149431 A1 | 8/2003 | Varieur |
| 2003/0153912 A1 | 8/2003 | Graf |
| 2003/0163133 A1 | 8/2003 | Altarac et al. |
| 2003/0176861 A1 | 9/2003 | Reed |
| 2004/0006342 A1 | 1/2004 | Altarac et al. |
| 2004/0024464 A1 | 2/2004 | Errico et al. |
| 2004/0039384 A1 | 2/2004 | Boehm et al. |
| 2004/0111088 A1 | 6/2004 | Picetti et al. |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0157186 A1 | 8/2004 | Abels et al. |
| 2004/0162558 A1 | 8/2004 | Hegde et al. |
| 2004/0172022 A1 | 9/2004 | Landry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0199169 A1 | 10/2004 | Koons et al. |
| 2004/0225292 A1 | 11/2004 | Sasso et al. |
| 2004/0230192 A1 | 11/2004 | Graf |
| 2004/0236330 A1 | 11/2004 | Purcell et al. |
| 2004/0249378 A1 | 12/2004 | Saint et al. |
| 2004/0249380 A1 | 12/2004 | Glascott |
| 2004/0267264 A1 | 12/2004 | Konieczynski et al. |
| 2005/0033298 A1 | 2/2005 | Hawkes et al. |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0080415 A1 | 4/2005 | Keyer et al. |
| 2005/0080420 A1 | 4/2005 | Farris et al. |
| 2005/0143737 A1 | 6/2005 | Pafford et al. |
| 2005/0154389 A1 | 7/2005 | Selover et al. |
| 2005/0154391 A1 | 7/2005 | Doherty et al. |
| 2005/0171537 A1 | 8/2005 | Mazel et al. |
| 2005/0171542 A1 | 8/2005 | Biedermann et al. |
| 2005/0177154 A1 | 8/2005 | Moumene et al. |
| 2005/0177166 A1 | 8/2005 | Timm et al. |
| 2005/0177179 A1 | 8/2005 | Baynham et al. |
| 2005/0187548 A1 | 8/2005 | Butler et al. |
| 2005/0192571 A1 | 9/2005 | Abdelgany |
| 2005/0203515 A1 | 9/2005 | Doherty et al. |
| 2005/0203516 A1 | 9/2005 | Biedermann et al. |
| 2005/0209592 A1 | 9/2005 | Schlapfer et al. |
| 2005/0216001 A1 | 9/2005 | David |
| 2005/0216003 A1 | 9/2005 | Biedermann et al. |
| 2005/0228378 A1 | 10/2005 | Kalfas et al. |
| 2005/0228385 A1 | 10/2005 | Iott et al. |
| 2005/0234421 A1 | 10/2005 | Mishima et al. |
| 2005/0234451 A1 | 10/2005 | Markworth |
| 2005/0261687 A1 | 11/2005 | Garamszegi et al. |
| 2005/0277928 A1 | 12/2005 | Boschert |
| 2005/0283157 A1 | 12/2005 | Coates et al. |
| 2005/0288671 A1 | 12/2005 | Yuan et al. |
| 2006/0004357 A1 | 1/2006 | Lee et al. |
| 2006/0025767 A1 | 2/2006 | Khalili |
| 2006/0025770 A1 | 2/2006 | Schlapfer et al. |
| 2006/0036252 A1 | 2/2006 | Baynham et al. |
| 2006/0052818 A1 | 3/2006 | Drake et al. |
| 2006/0064091 A1 | 3/2006 | Ludwig et al. |
| 2006/0079892 A1 | 4/2006 | Roychowdhury et al. |
| 2006/0084993 A1 | 4/2006 | Andry et al. |
| 2006/0084995 A1 | 4/2006 | Biedermann et al. |
| 2006/0084996 A1 | 4/2006 | Metz-Stavenhagen |
| 2006/0089634 A1 | 4/2006 | Anderson et al. |
| 2006/0089643 A1 | 4/2006 | Mujwid |
| 2006/0100622 A1 | 5/2006 | Jackson |
| 2006/0106383 A1 | 5/2006 | Biedermann et al. |
| 2006/0111779 A1 | 5/2006 | Petersen |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149233 A1 | 7/2006 | Richelsoph |
| 2006/0149241 A1 | 7/2006 | Richelsoph et al. |
| 2006/0149244 A1 | 7/2006 | Amrein et al. |
| 2006/0149265 A1 | 7/2006 | James et al. |
| 2006/0155277 A1 | 7/2006 | Metz-Stavenhagen |
| 2006/0173456 A1 | 8/2006 | Hawkes et al. |
| 2006/0200131 A1 | 9/2006 | Chao et al. |
| 2006/0212034 A1 | 9/2006 | Triplett et al. |
| 2006/0217717 A1 | 9/2006 | Whipple |
| 2006/0229611 A1 | 10/2006 | Avery et al. |
| 2006/0235385 A1 | 10/2006 | Whipple |
| 2006/0235393 A1 | 10/2006 | Bono et al. |
| 2006/0241594 A1 | 10/2006 | McCarthy et al. |
| 2006/0241599 A1 | 10/2006 | Konieczynski et al. |
| 2006/0241624 A1 | 10/2006 | Kizuka et al. |
| 2006/0247636 A1 | 11/2006 | Yuan et al. |
| 2006/0247668 A1 | 11/2006 | Park |
| 2006/0271047 A1 | 11/2006 | Jackson |
| 2006/0282080 A1 | 12/2006 | Todd et al. |
| 2006/0293659 A1 | 12/2006 | Alvarez |
| 2006/0293664 A1 | 12/2006 | Schumacher |
| 2007/0016200 A1 | 1/2007 | Jackson |
| 2007/0043365 A1* | 2/2007 | Ritland ............... A61B 17/7011 606/257 |
| 2007/0049932 A1 | 3/2007 | Richelsoph et al. |
| 2007/0055240 A1 | 3/2007 | Matthis et al. |
| 2007/0088357 A1 | 4/2007 | Johnson et al. |
| 2007/0090238 A1 | 4/2007 | Justis |
| 2007/0118118 A1 | 5/2007 | Kwak et al. |
| 2007/0118121 A1 | 5/2007 | Purcell et al. |
| 2007/0118123 A1 | 5/2007 | Strausbaugh et al. |
| 2007/0123860 A1 | 5/2007 | Francis et al. |
| 2007/0123870 A1 | 5/2007 | Jeon et al. |
| 2007/0135817 A1 | 6/2007 | Ensign |
| 2007/0161987 A1 | 7/2007 | Capote et al. |
| 2007/0161994 A1 | 7/2007 | Lowery et al. |
| 2007/0167946 A1* | 7/2007 | Triplett ............... A61B 17/7064 606/279 |
| 2007/0167949 A1 | 7/2007 | Altarac et al. |
| 2007/0179501 A1 | 8/2007 | Firkins |
| 2007/0191844 A1 | 8/2007 | Carls et al. |
| 2007/0198014 A1 | 8/2007 | Graf et al. |
| 2007/0225711 A1 | 9/2007 | Ensign |
| 2007/0233087 A1 | 10/2007 | Schlapfer |
| 2007/0233091 A1 | 10/2007 | Naifeh et al. |
| 2007/0246614 A1 | 10/2007 | Allmann et al. |
| 2007/0250061 A1 | 10/2007 | Chin et al. |
| 2007/0250064 A1 | 10/2007 | Darois et al. |
| 2007/0270805 A1 | 11/2007 | Miller et al. |
| 2007/0270817 A1 | 11/2007 | Rezach |
| 2007/0270820 A1 | 11/2007 | Dickinson et al. |

(56) References Cited

U.S. PATENT DOCUMENTS

| | | |
|---|---|---|
| 2007/0270880 A1 | 11/2007 | Lindemann et al. |
| 2007/0282339 A1 | 12/2007 | Schwab |
| 2007/0288004 A1 | 12/2007 | Alvarez |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0058805 A1 | 3/2008 | Stuart |
| 2008/0058812 A1 | 3/2008 | Zehnder |
| 2008/0086126 A1 | 4/2008 | Miller |
| 2008/0103502 A1 | 5/2008 | Capote et al. |
| 2008/0140075 A1 | 6/2008 | Ensign et al. |
| 2008/0140135 A1 | 6/2008 | Konieczynski et al. |
| 2008/0154277 A1 | 6/2008 | Machalk et al. |
| 2008/0154308 A1 | 6/2008 | Sherman et al. |
| 2008/0177260 A1 | 7/2008 | McKinley et al. |
| 2008/0177323 A1 | 7/2008 | Null et al. |
| 2008/0188260 A1 | 8/2008 | Xiao et al. |
| 2008/0208257 A1 | 8/2008 | Matthys |
| 2008/0215095 A1 | 9/2008 | Biedermann et al. |
| 2008/0234743 A1 | 9/2008 | Marik |
| 2008/0243185 A1 | 10/2008 | Felix et al. |
| 2008/0249570 A1 | 10/2008 | Carson et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0294194 A1* | 11/2008 | Capote .............. A61B 17/7037 606/100 |
| 2008/0294202 A1 | 11/2008 | Peterson et al. |
| 2008/0306553 A1 | 12/2008 | Zucherman et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2009/0105770 A1 | 4/2009 | Berrevoets et al. |
| 2009/0149887 A1 | 6/2009 | Schlaepfer et al. |
| 2009/0163955 A1* | 6/2009 | Moumene ............ A61B 17/701 606/257 |
| 2009/0177231 A1* | 7/2009 | Kiester .............. A61B 17/705 606/252 |
| 2009/0187217 A1 | 7/2009 | Weiman et al. |
| 2009/0198279 A1 | 8/2009 | Zhang et al. |
| 2009/0198280 A1 | 8/2009 | Spratt et al. |
| 2009/0222042 A1 | 9/2009 | Firkins et al. |
| 2009/0259256 A1 | 10/2009 | Miller |
| 2009/0270916 A1 | 10/2009 | Ramsay et al. |
| 2010/0004694 A1 | 1/2010 | Little |
| 2010/0042165 A1 | 2/2010 | Aflatoon |
| 2010/0057125 A1 | 3/2010 | Viker |
| 2010/0087864 A1 | 4/2010 | Klein et al. |
| 2010/0094345 A1 | 4/2010 | Saidha et al. |
| 2010/0145394 A1 | 6/2010 | Harvey et al. |
| 2010/0168797 A1 | 7/2010 | Graf |
| 2010/0191286 A1 | 7/2010 | Butler |
| 2010/0198272 A1 | 8/2010 | Keyer et al. |
| 2010/0241172 A1 | 9/2010 | Biyani et al. |
| 2010/0249843 A1 | 9/2010 | Wegrzyn, III |
| 2010/0276051 A1 | 11/2010 | Kanehira |
| 2010/0292736 A1 | 11/2010 | Schwab |
| 2010/0298890 A1 | 11/2010 | Marino |
| 2010/0305621 A1 | 12/2010 | Wang et al. |
| 2010/0313428 A1 | 12/2010 | Mocanu |
| 2010/0318131 A1* | 12/2010 | James ............... A61B 17/7007 606/279 |
| 2010/0324599 A1 | 12/2010 | Montello et al. |
| 2011/0087289 A1 | 4/2011 | Pham et al. |
| 2011/0106166 A1 | 5/2011 | Keyer et al. |
| 2011/0118791 A1 | 5/2011 | Nunley et al. |
| 2011/0172717 A1 | 7/2011 | Miller |
| 2011/0213424 A1 | 9/2011 | Biedermann et al. |
| 2011/0230917 A1 | 9/2011 | Carson et al. |
| 2011/0270325 A1 | 11/2011 | Keyer et al. |
| 2011/0276051 A1 | 11/2011 | Blakemore et al. |
| 2012/0010629 A1 | 1/2012 | Mire et al. |
| 2012/0089194 A1 | 4/2012 | Strausbaugh et al. |
| 2012/0101533 A1 | 4/2012 | Purcell et al. |
| 2012/0109200 A1 | 5/2012 | Cahill et al. |
| 2012/0265249 A1 | 10/2012 | Fielding et al. |
| 2013/0012955 A1 | 1/2013 | Lin |
| 2013/0012995 A1 | 1/2013 | Butterfield et al. |
| 2013/0018421 A1 | 1/2013 | George et al. |
| 2013/0079827 A1 | 3/2013 | Neary et al. |
| 2013/0261680 A1 | 10/2013 | Baccelli et al. |
| 2013/0268011 A1 | 10/2013 | Rezach et al. |
| 2018/0036041 A1 | 2/2018 | Pham et al. |

FOREIGN PATENT DOCUMENTS

| | | |
|---|---|---|
| CN | 102458279 A | 5/2012 |
| DE | 9314297 U1 | 4/1994 |
| DE | 4329220 A1 | 3/1995 |
| DE | 29903342 U1 | 6/1999 |
| DE | 29810798 U1 | 10/1999 |
| DE | 19912364 A1 | 10/2000 |
| DE | 20207785 U1 | 9/2003 |
| EP | 0408489 B1 | 9/1994 |
| EP | 0674880 A1 | 10/1995 |
| EP | 0828459 A1 | 3/1998 |
| EP | 0837656 A1 | 4/1998 |
| EP | 0612507 B1 | 12/1998 |
| EP | 0683644 B1 | 6/2000 |
| EP | 1198205 A1 | 4/2002 |
| EP | 1210914 A1 | 6/2002 |
| EP | 0807420 B1 | 7/2002 |
| EP | 1248573 A1 | 10/2002 |
| EP | 1269929 A1 | 1/2003 |
| EP | 1316295 A2 | 6/2003 |
| EP | 1323391 A2 | 7/2003 |
| EP | 1637085 A2 | 3/2006 |
| EP | 1313403 B1 | 10/2006 |
| EP | 1741396 A1 | 1/2007 |
| EP | 1665994 B1 | 6/2008 |
| EP | 1928358 A2 | 6/2008 |
| EP | 1961392 A1 | 8/2008 |
| EP | 2052690 A1 | 4/2009 |
| EP | 1294297 B1 | 8/2010 |
| GB | 0820252 | 9/1959 |
| GB | 2414674 B | 8/2009 |
| GB | 2465156 A | 5/2010 |
| JP | 06-154258 | 6/1994 |
| JP | 08-112291 A | 5/1996 |
| JP | 2005-510286 | 4/2005 |
| JP | 2006-508748 A | 3/2006 |
| JP | 2006-154258 | 6/2006 |
| JP | 2006-525102 | 11/2006 |
| JP | 2009-535114 A | 10/2009 |
| JP | 2012-523927 A | 10/2012 |
| JP | 2012-530550 A | 12/2012 |
| KR | 10-2008-0112851 A | 12/2008 |
| KR | 10-0896043 B1 | 5/2009 |
| KR | 10-2012-0013312 A | 2/2012 |
| KR | 10-2012-0039622 A | 4/2012 |
| WO | 94/17736 A1 | 8/1994 |
| WO | 96/32071 A1 | 10/1996 |
| WO | 97/02786 A1 | 1/1997 |
| WO | 98/08454 | 3/1998 |
| WO | 98/52482 A1 | 11/1998 |
| WO | 2000/015125 A1 | 3/2000 |
| WO | 00/21455 A1 | 4/2000 |
| WO | 01/06940 A1 | 2/2001 |
| WO | 01/52758 A1 | 7/2001 |
| WO | 02/00124 A1 | 1/2002 |
| WO | 02/17803 A2 | 3/2002 |
| WO | 02/76314 A1 | 10/2002 |
| WO | 2003/045261 A1 | 6/2003 |
| WO | 2004/052218 A1 | 6/2004 |
| WO | 2004/089245 A2 | 10/2004 |
| WO | 2004/098425 A2 | 11/2004 |
| WO | 2005/016161 A1 | 2/2005 |
| WO | 2006/088452 A2 | 8/2006 |
| WO | 2006/114437 A1 | 11/2006 |
| WO | 2006/116437 A2 | 11/2006 |
| WO | 2006/135555 A2 | 12/2006 |
| WO | 2007/038350 A2 | 4/2007 |
| WO | 2007/040824 A2 | 4/2007 |
| WO | 2007/045892 A1 | 4/2007 |

(56) References Cited

FOREIGN PATENT DOCUMENTS

| | | |
|---|---|---|
| WO | 2007/047711 A2 | 4/2007 |
| WO | 2007/127632 A2 | 11/2007 |
| WO | 2007/146032 A2 | 12/2007 |
| WO | 2008/027940 A1 | 3/2008 |
| WO | 2008/048953 A2 | 4/2008 |
| WO | 2008/069420 A1 | 6/2008 |
| WO | 2008/089096 A2 | 7/2008 |
| WO | 2008/146185 A1 | 12/2008 |
| WO | 2008/147663 A1 | 12/2008 |
| WO | 2009/001978 A1 | 12/2008 |
| WO | 2009/015100 A2 | 1/2009 |
| WO | 2010/030906 A1 | 3/2010 |
| WO | 2010/028287 A3 | 6/2010 |
| WO | 2010/120989 A1 | 10/2010 |
| WO | 2010/148231 A1 | 12/2010 |
| WO | 2012/154772 A2 | 11/2012 |

OTHER PUBLICATIONS

Aebi et al., "AO ASIF Principles in Spine Surgery", Springer, 1998, 186-190.
International Patent Application No. PCT/US2006/037120: International Search Report dated Jul. 11, 2007, 4 pages.
International Patent Application No. PCT/US2006/047986: International Search Report dated May 2, 2007, 2 pages.
International Patent Application No. PCT/US2010/031178: International Search Report dated Jun. 22, 2010, 8 pages.
International Patent Application No. PCT/US2010/031178: Notification of Transmittal of The International Preliminary Report on Patentability dated Jun. 14, 2011, 12 pages.
International Patent Application No. PCT/US2008/070670: International Search Report dated Feb. 17, 2009, 3 pages.
International Patent Application No. PCT/US2008/070670; International Preliminary Report on Patentability, Jul. 9, 2009, 6 pages.
International Patent Application No. PCT/US2009/056692: International Search Report and Written Opinion dated Dec. 3, 2009, 14 pages.
International Patent Application No. PCT/US2010/039037: International Preliminary Report on Patentability dated Jul. 11, 2011, 14 pages.
International Patent Application No. PCT/US2010/039037: International Search Report Dated Jan. 9, 2010, 5 pages.
International Preliminary Report on Patentability issued on Dec. 4, 2011 in application PCT/US2009/058788 7pgs.
International Preliminary Report on Patentability issued on May 3, 2011 in PCT application PCT/US2009/063056.
U.S. Provisional Application Filed on Apr. 15, 2009 by Nicholas Theodore et al., entitled "Revision Connector for Spinal Constructs", U.S. Appl. No. 61/169,336.
U.S. Provisional Application Filed on Jun. 17, 2009 by Albert Montello et al., entitled Top-Loading Polyaxial Construct Extender for Spinal Surgery, U.S. Appl. No. 61/187,902.

* cited by examiner

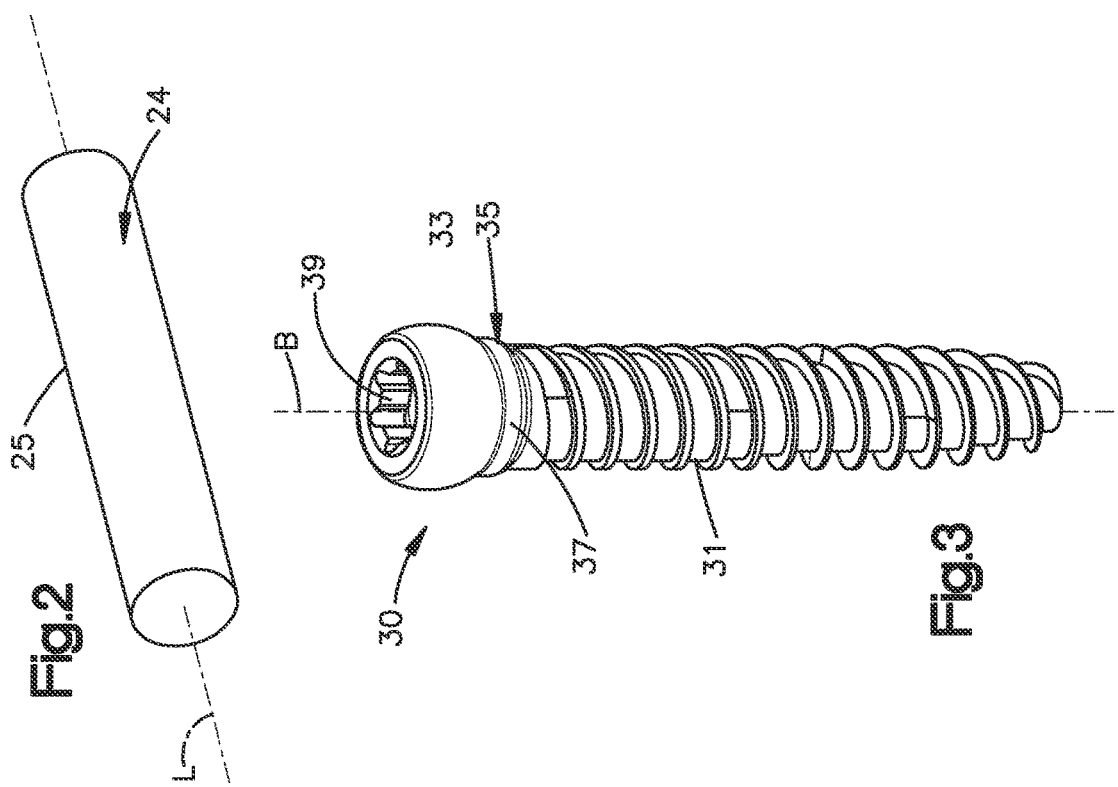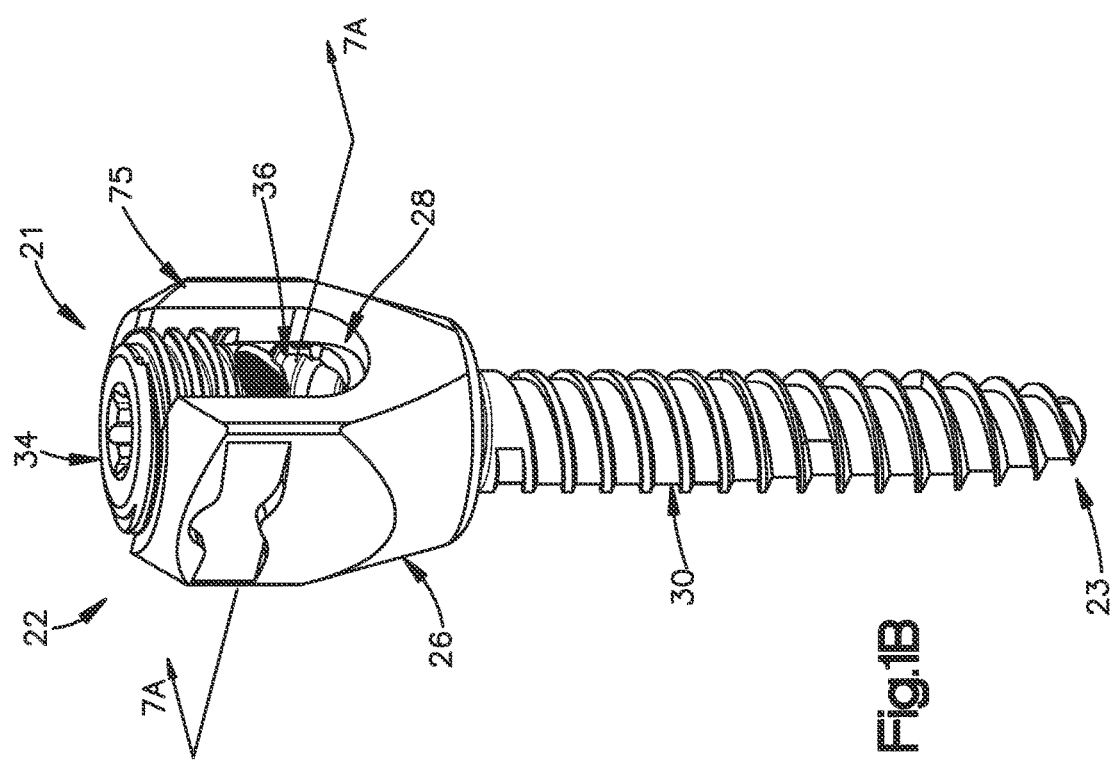

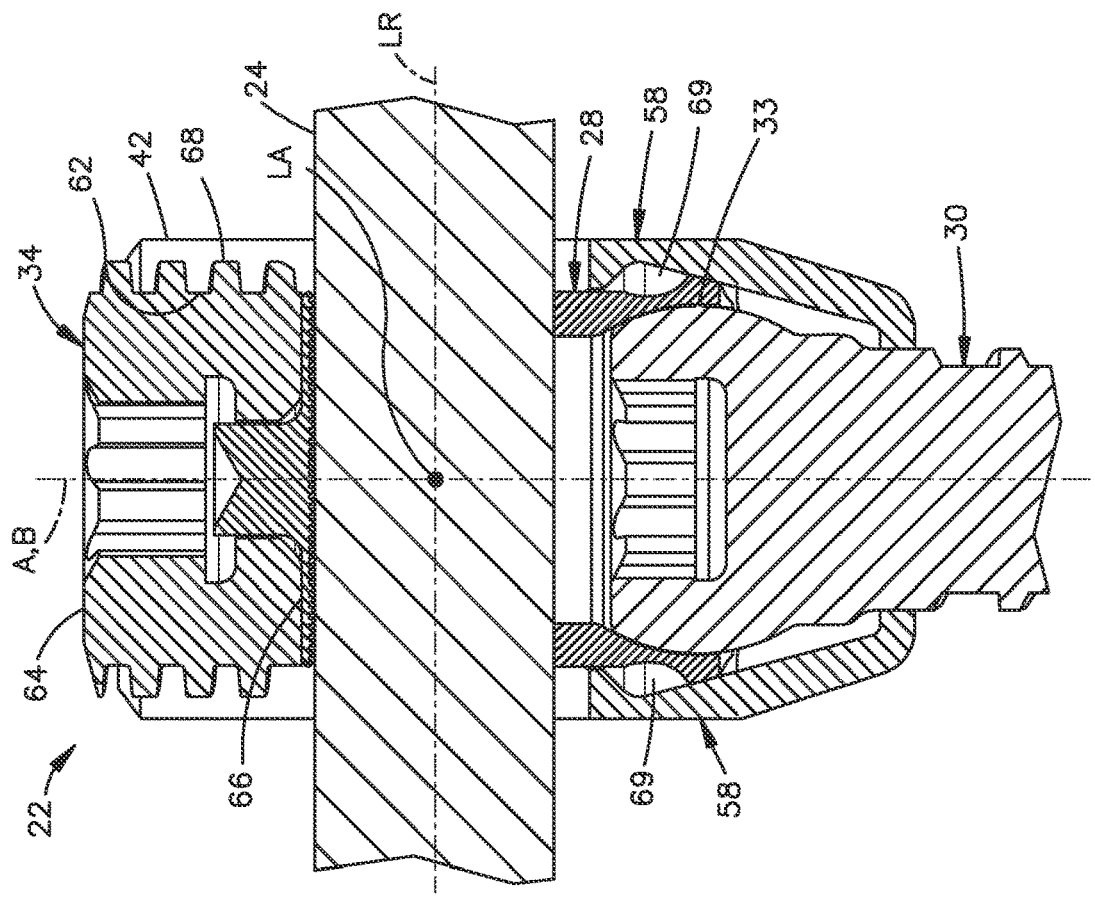
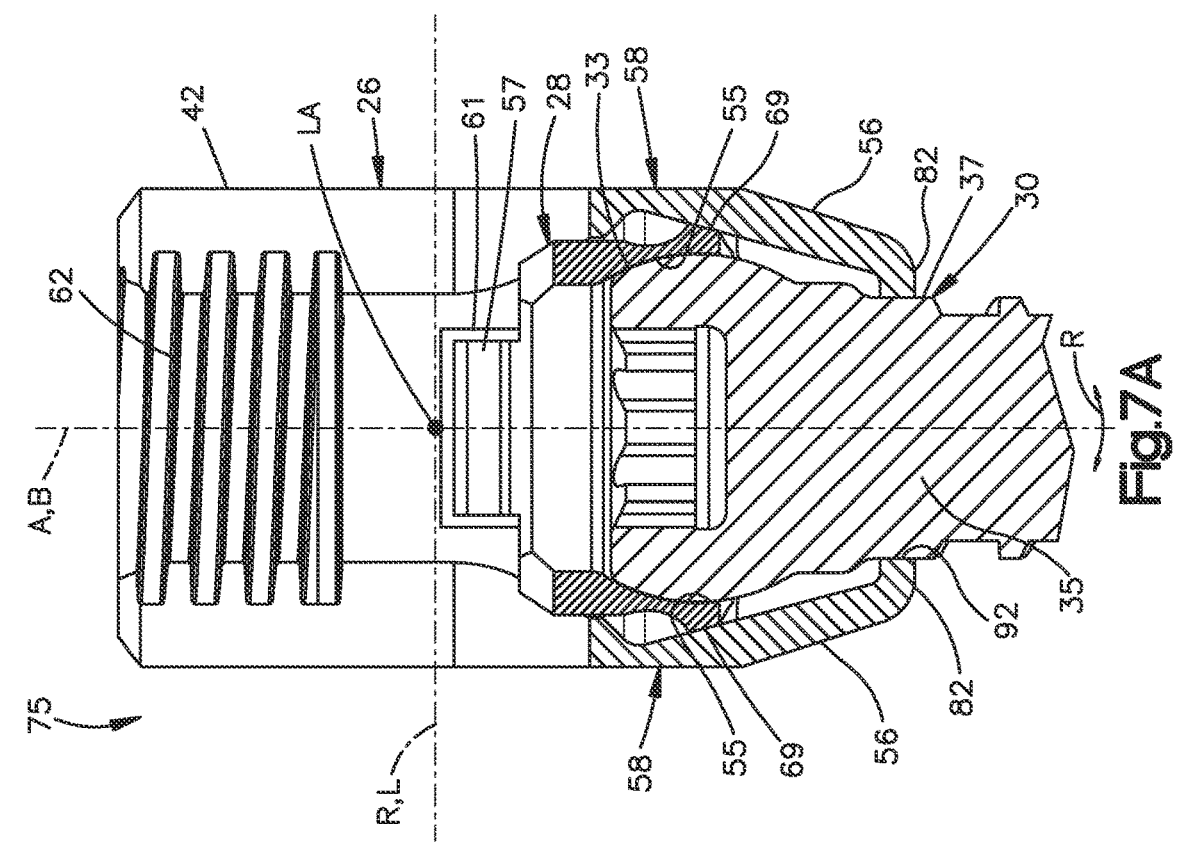

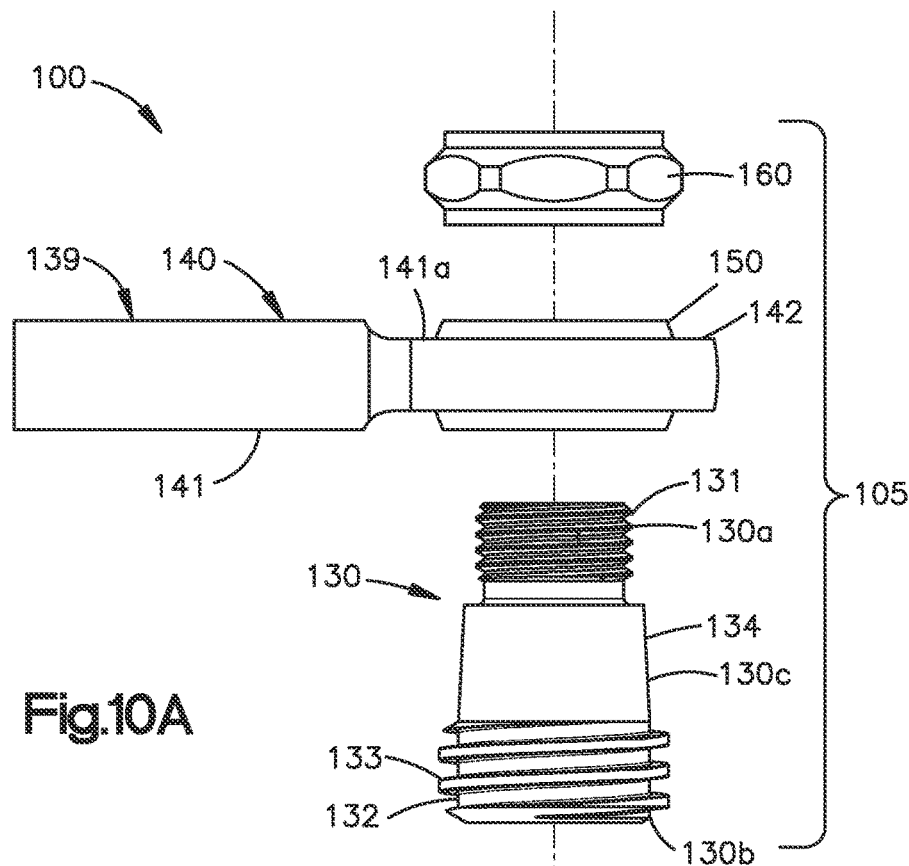
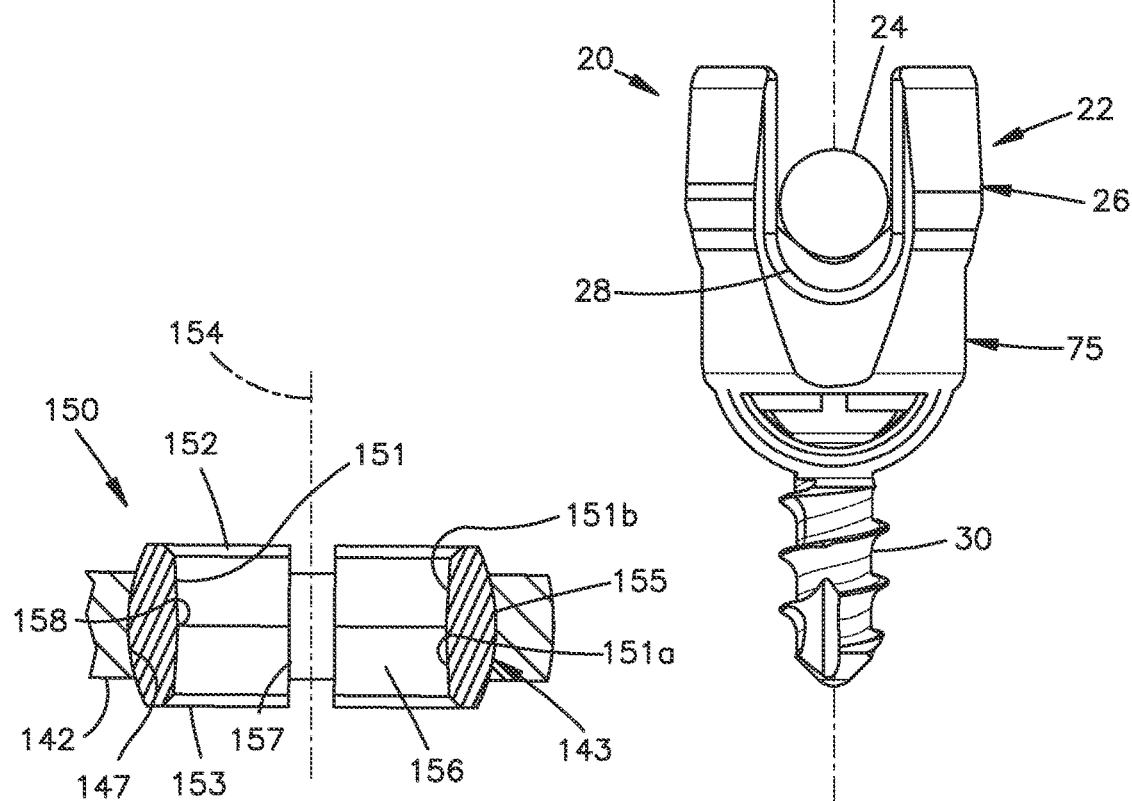
Fig.10A
Fig.10B

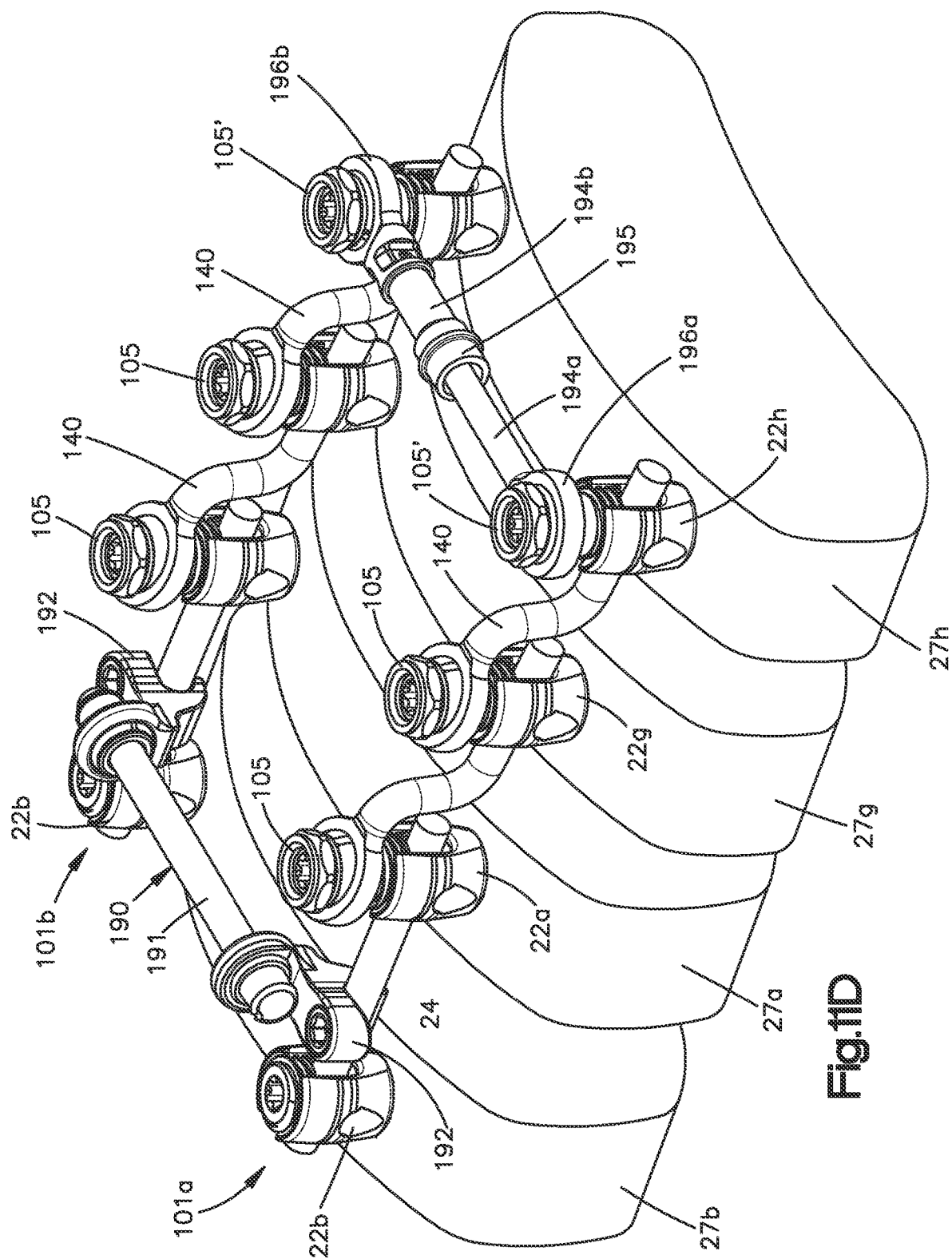

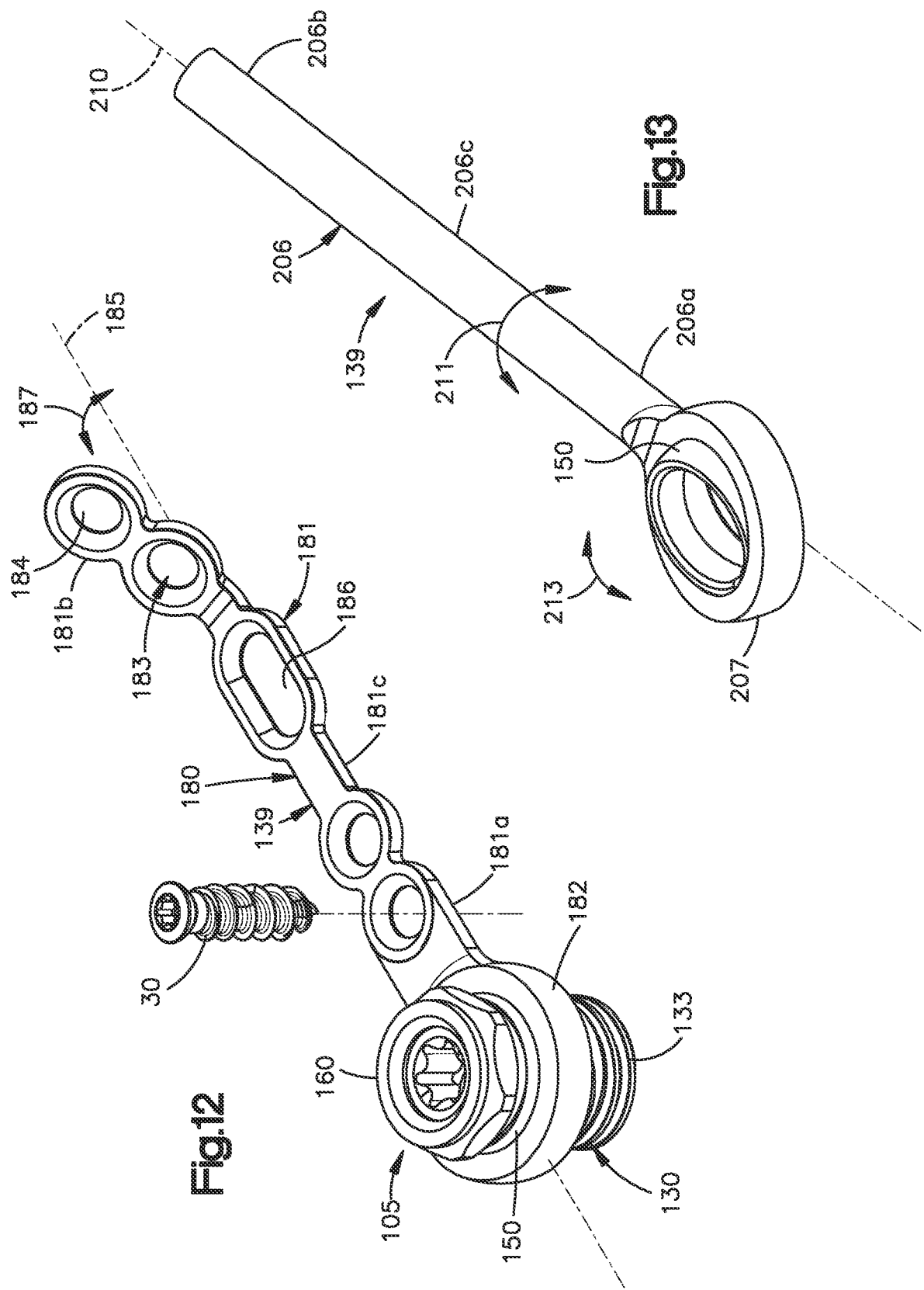

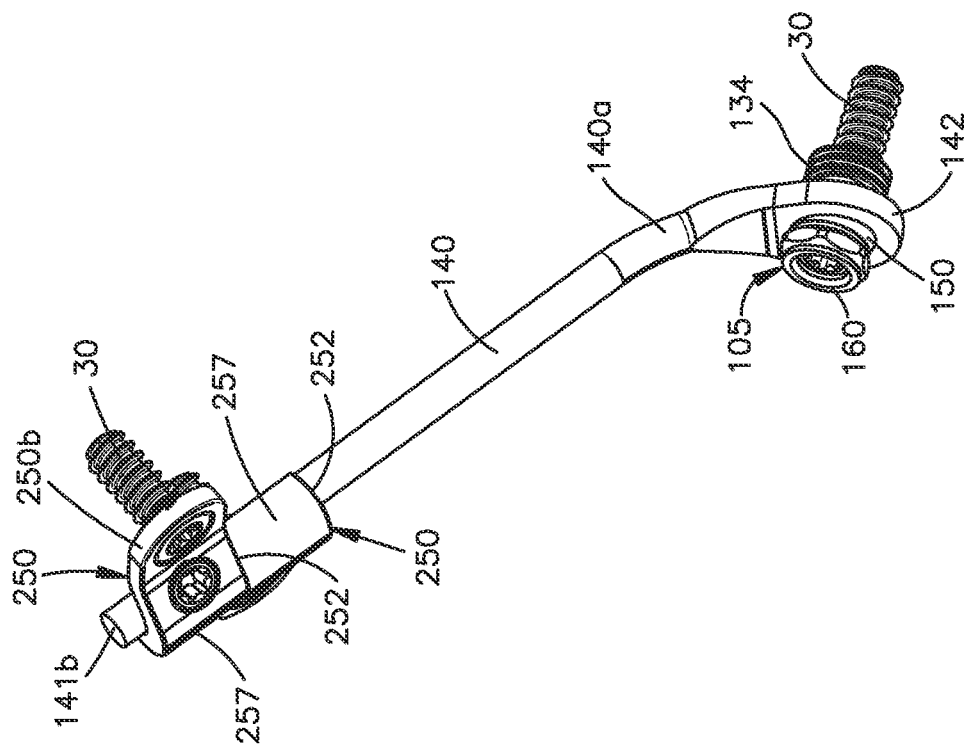
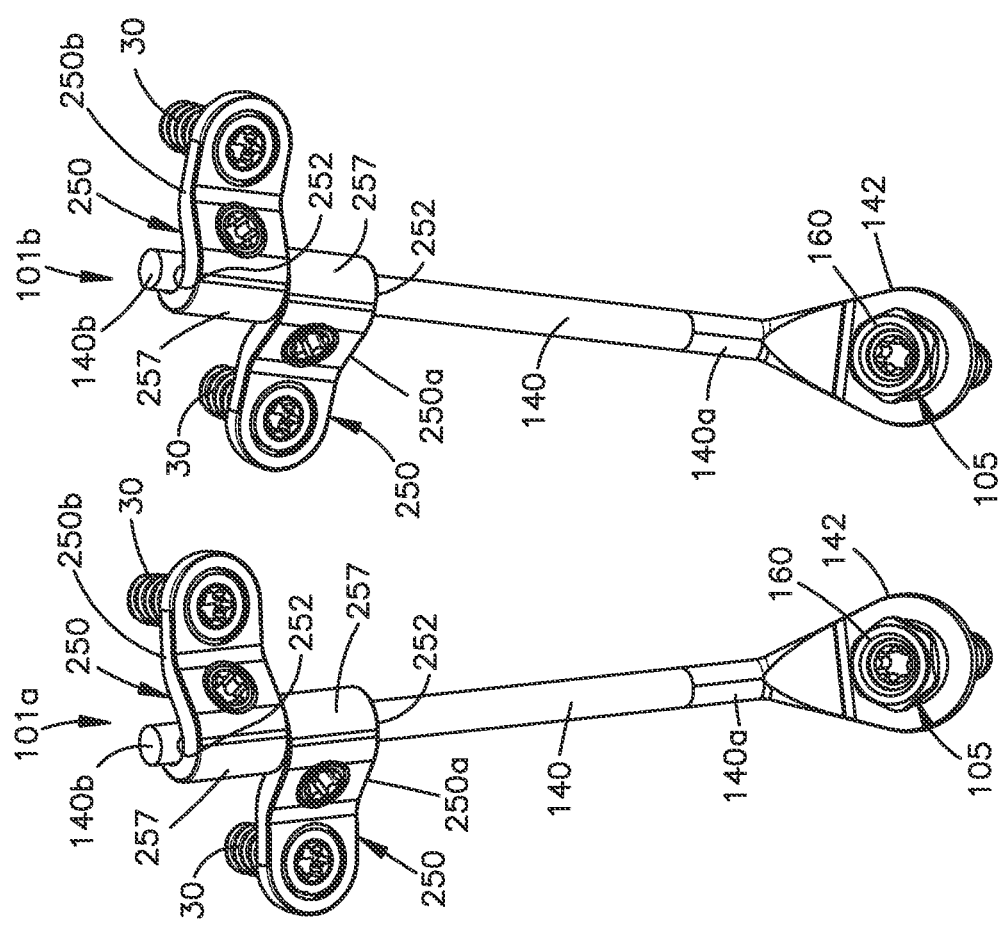

REVISION CONNECTOR FOR SPINAL CONSTRUCTS

CROSS-REFERENCE TO RELATED APPLICATIONS

This Application is a continuation of U.S. patent application Ser. No. 15/349,509, filed Nov. 11, 2016, which is a continuation of U.S. patent application Ser. No. 12/817,920, filed Jun. 17, 2010, which claims the benefit of U.S. Provisional Application Ser. No. 61/187,902, filed Jun. 17, 2009, the disclosures of both of which are hereby incorporated by reference as if set forth in their entirety herein.

TECHNICAL FIELD

The present disclosure relates generally to orthopedics, and in particular relates to implants and methods for extending existing posterior vertebral screw assemblies to additional levels.

BACKGROUND

The options that exist for revising and/or extending a posterior vertebral screw and rod construct in a patient are limited. Patients who have undergone previous spinal surgery often develop symptoms in adjacent spinal levels, which often cause pain and require additional surgery. Such additional spine surgeries often require existing hardware constructs to be extended one or more additional spinal levels. In such cases, a surgeon must decide if he can 1) extend the construct using the same hardware as the patient's existing hardware, 2) extend the construct using different hardware while leaving some of the patient's existing hardware in tact, or 3) remove all of the patient's existing hardware and replace it with new hardware, including the new spinal levels to be instrumented. Several disadvantages, however, characterize these approaches.

First, the patient's existing hardware must be identified via X-rays or fluoroscopy and, once identified, the surgeon must determine if the same make and model of hardware is available to the hospital or still on the market. The surgeon must also determine if his experience will allow him to revise and the existing hardware and/or add on new hardware, as some existing hardware systems are more difficult to revise or install. Based on these determinations, the surgeon may decide to revise using new hardware. Although a surgeon can choose the hardware of his choice, a connection between the existing hardware and the new hardware must be made, most often accomplished by creating a long incision long enough to uncover all previously fixed vertebral bodies along with the new vertebral body or bodies to be fixed, removing the underlying rod, implanting the new screws, and then inserting a new rod to the previously implanted rod and the newly implanted rod. Concerns exist, however, that such a technique may disturb certain spinal levels that were previously asymptomatic and, thus, results in pain that previously did not exist. Further, many verterbal screw systems are not compatible with one another, significantly limiting the new hardware options for adding to the existing construct. If the surgeon decides to remove all existing hardware and replace it with new hardware of his choice he again is disturbing some spinal levels that were previously asymptomatic. Each of these options for adding and replacing hardware is time-consuming, especially if the surgeon is unfamiliar with the patient's existing hardware.

SUMMARY

In accordance with one embodiment, an extender system is configured to be operatively coupled to a vertebral implant that is secured to a vertebra, the vertebral implant including a first bone anchor and a first anchor seat that receives the first bone anchor. The extender system includes an extension member including a body and an engagement member coupled to the body. The extender system further includes a fastener that is configured to couple the extension member to the vertebral implant. The extender system further includes a second bone anchor that is configured to attach the extension member to an underlying bone disposed adjacent the vertebra.

BRIEF DESCRIPTION OF THE DRAWINGS

The foregoing summary, as well as the following detailed description of preferred embodiments of the application, will be better understood when read in conjunction with the appended drawings. For the purposes of illustrating the revision connector devices of the present application, there is shown in the drawings preferred embodiments. It should be understood, however, that the application is not limited to the precise arrangements and instrumentalities shown. In the drawings:

FIG. 1B is a perspective view of one of the bone fixation elements illustrated in FIG. 1A constructed in accordance with one embodiment, including an anchor seat, a bone anchor, a collet, and a locking cap;

FIG. 2 is a perspective view of the spine fixation rod illustrated in FIG. 1A;

FIG. 3 is a perspective view of the bone anchor illustrated in FIG. 1B;

FIG. 7A is a sectional side elevation view of the bone fixation element illustrated in FIG. 1B taken along line 7A-7A, with the locking cap removed, to illustrate a vertebral screw assembly;

FIG. 7B is a sectional side elevation view similar to FIG. 7B, but showing a spine fixation rod extending through the anchor seat, and a locking cap affixed to the anchor seat;

FIG. 10A is an exploded view of an extender system constructed in accordance with one embodiment;

FIG. 10B is a sectional view through a portion of the extender system illustrated in FIG. 10A;

FIG. 11D is a perspective view of the fixation elements connected by a cross bar and implanted into a plurality of schematically illustrated vertebrae FIG. 12 is a perspective view of the extender system illustrated in FIG. 10A, but including an extension member constructed in accordance with an alternative embodiment;

FIG. 13 is a perspective view of the extender system illustrated in FIG. 10A, configured to connect a bone fixation element to a previously-implanted translaminar screw;

FIG. 14A is a perspective view of a pair of the extender systems illustrated in FIG. 10A configured to connect an occiput to a spine;

FIG. 14B is another perspective view of one of the extender systems illustrated in FIG. 14A;

DETAILED DESCRIPTION

Figure 1A:
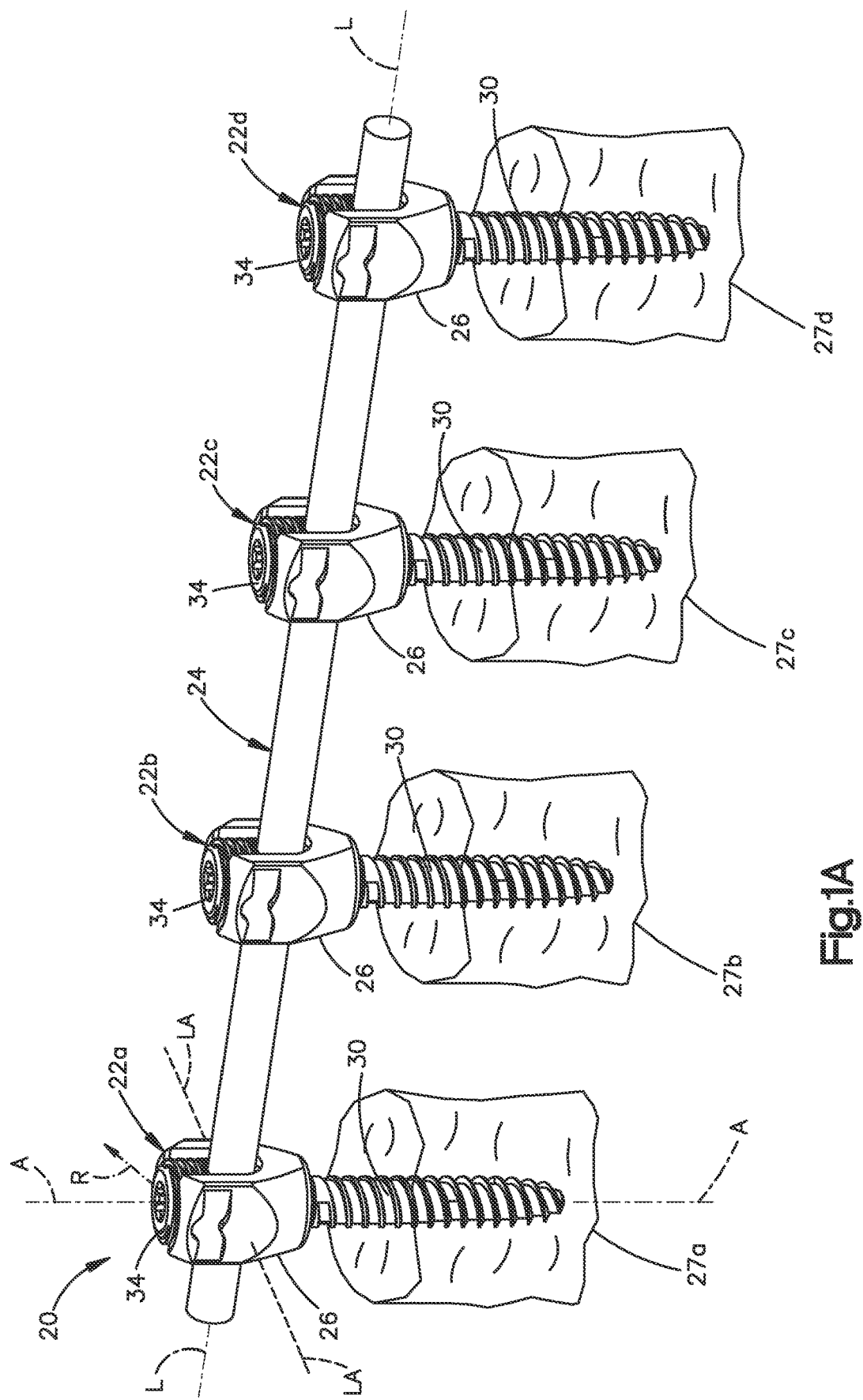
FIG. 1A is a perspective view of a bone fixation assembly constructed in accordance with one embodiment including a plurality of bone fixation elements connected to a previously implanted spine fixation rod, and illustrated schematically as each being previously secured to a vertebra.

Certain terminology may be used in the following description for convenience only and should not be considered as limiting in any way. For instance, a bone fixation assembly 20 includes one or more bone fixation elements 22, and four bone fixation elements 22A-D as illustrated in FIG. 1A. As shown in FIG. 1B, each bone fixation element 22 extends vertically along an axial direction A, and generally horizontally along a radial direction R that extends perpendicular to the axial direction A. Thus, the radial direction R includes a longitudinal direction L and a lateral direction LA that extends perpendicular to the longitudinal direction L. It should be appreciated that the directional terms "longitudinal," "lateral," can likewise apply to the bone fixation assembly 20 as extending horizontally, and the directional term "transverse" can refer to a vertical direction. The bone fixation element 22 defines an upper or posterior end 21 and a lower or inferior end 23, such that the directional terms "upper" and "lower" and derivatives thereof refer to a direction from the lower end 23 towards the upper end 21, and from the upper end 21 towards the lower end 23, respectively.

The words "inward," "outward," "upper," "lower," "distal," and "proximal," refer to directions toward or away from, respectively, the geometric center of the bone fixation assembly 20 and its components. The words, "anterior", "posterior", "superior," "inferior" and related words and/or phrases designate preferred positions and orientations in the human body to which reference is made and are not meant to be limiting. It should further be appreciated that while round structures define diameters as described herein, the round structures could be replaced with alternative (e.g., polygonal) structures which would define alternative cross-sectional dimensions opposed to diameters. The term "diameter" as used herein is intended to include all such alternatives unless otherwise specified. The terminology includes the above-listed words, derivatives thereof and words of similar import.

It should be appreciated that the directional terms are used herein with reference to the orientation of the bone fixation assembly 20 and its components as illustrated, and that the actual orientation of the bone fixation assembly 20 and its components may change during use. For instance, the axial direction is illustrated as extending along a vertical direction, and the radial direction is illustrated as extending along a horizontal direction, however the directions that encompass the various directions may differ during use, depending, for instance, on the desired orientation of the bone fixation assembly 20 during use. Accordingly, the directional terms are used herein merely for the purposes of clarity and convenience only, in a non-limiting manner.

Referring now to FIG. 1A, the bone fixation assembly 20 includes a plurality of bone fixation elements, such as bone fixation elements 22A-D, connected by a spine fixation rod 24 that extends along a longitudinal axis L. The bone fixation elements 22A-D each include a bone anchor 30 that is implanted (e.g., screwed) into a corresponding vertebra 27A-D. The bone fixation elements 22A-D can be implanted into the posterior region of the spine, or any suitable alternative region of the spine, for instance into the pedicle or other spinal region. The bone anchor 30 can be provided as a screw, hook, or alternatively constructed top loading bone anchor configured to attach to an underlying vertebra. Unless otherwise specified, the bone fixation assembly 20 and its components can be made from titanium-aluminum-niobium alloy (TAN), implant-grade 316L stainless steel, or any suitable alternative implant-grade material.

With continuing reference to FIG. 1A, the bone fixation elements 22A-D will be described as and may be generally implanted in the spine, for instance at the posterior portion of a lumbar, thoracic, or cervical vertebral body. In this regard, when the bone fixation elements 22A-D are joined by the rod 24, the assembly 20 fixes the relative position of the vertebrae (illustrated schematically at 27A-D). Accordingly, the bone fixation elements 22A-D can be referred to as vertebral implants, the spine fixation rod 24 can be referred to as a spine fixation rod, and the bone fixation assembly 20 can be referred to as a vertebral implant. However, it should be appreciated that the bone fixation assembly 20 can also be used for fixation of other parts of the body, such as joints, long bones, or bones in the hands, face, feet, extremities, cranium, and the like.

As shown in FIG. 2, the spine fixation rod 24 is elongate along a longitudinal axis L, and includes a body 25 that is cylindrical or tubular in shape. The longitudinal axis L extends generally in a cranial-caudal direction when the bone fixation assembly is affixed to the spine. The rod body 25 may include, but is not limited to, a solid body, a non-solid body, a flexible or dynamic body, or the like, and can assume any alternative shape as desired. It should thus be appreciated that the bone fixation assembly 20 is not limited in use to any particular spine fixation rod 24.

Referring now also to FIG. 1B, the bone fixation elements 22a-d of the bone fixation assembly 20 will now be described with respect to the bone fixation element 22. In particular, the bone fixation element 22 generally includes a vertebral implant 75, and a locking cap 34. The vertebral implant 75 is illustrated as including a bone anchor seat 26, a collet 28 disposed inside the anchor seat 26, a bone anchor 30 (shown as a threaded bone screw) having a head portion 33 (see FIG. 3) attached to the collet 28. The locking cap 34 is installed in the anchor seat 26 at a location above the collet 28, such that the spine fixation rod 24 is located in a rod slot 36 that is disposed, and as illustrated defined, between the collet 28 and the locking cap 34.

Referring also to FIG. 3, the bone anchor 30 is configured as a bone screw, or vertebral screw; that includes an externally threaded shaft 31 coupled at its upper end to an enlarged curved head 33. The shaft 31 extends axially along a central axis B of rotation, and can define any suitable diameter, length, and thread design so as to engage the underlying bone, such as a vertebra 27. Alternatively, the shaft 31 can be unthreaded so as to define a pin or a nail if desired. Thus, one skilled in the art will appreciate that the bone anchor 30 is not limited to any particular type of shaft 31. The bone anchor 30 may also be cannulated and fenestrated such that openings extend radially outward from a central hollow channel in a cannulated shaft to urge fluid out of the bone anchor 30 during injection or draw fluid into the central hollow channel from the radial sides of the anchor during extraction of material adjacent the anchor if desired.

The bone anchor 30 further includes a vertically extending neck 35 connected between the shaft 31 and the head 33. The neck 35 is illustrated as extending axially in a direction parallel to axis B, and includes an outer neck surface 37 that defines a neck diameter, which is less than the diameter of the head 33.

The head 33 can define at least a partially spherical curvature, such as a semi-spherical curvature, or can alternatively define any suitable curvature as desired to facilitate rotation with respect to the collet 28 as is described in more detail below. The head 33 also includes a drive surface 39 configured to receive a corresponding tip of a drive tool, such as a screw driver configured to rotate the bone anchor 30 into engagement with the vertebrae 27 or other underlying bone surface. The drive surface 39 can define a hexagon, a star drive pattern, a Phillips head pattern, a slot for a screw driver, threads configured to receive corresponding threads of a threaded drive post, or any suitable drive tool engaging structure as desired.

Figure 4:
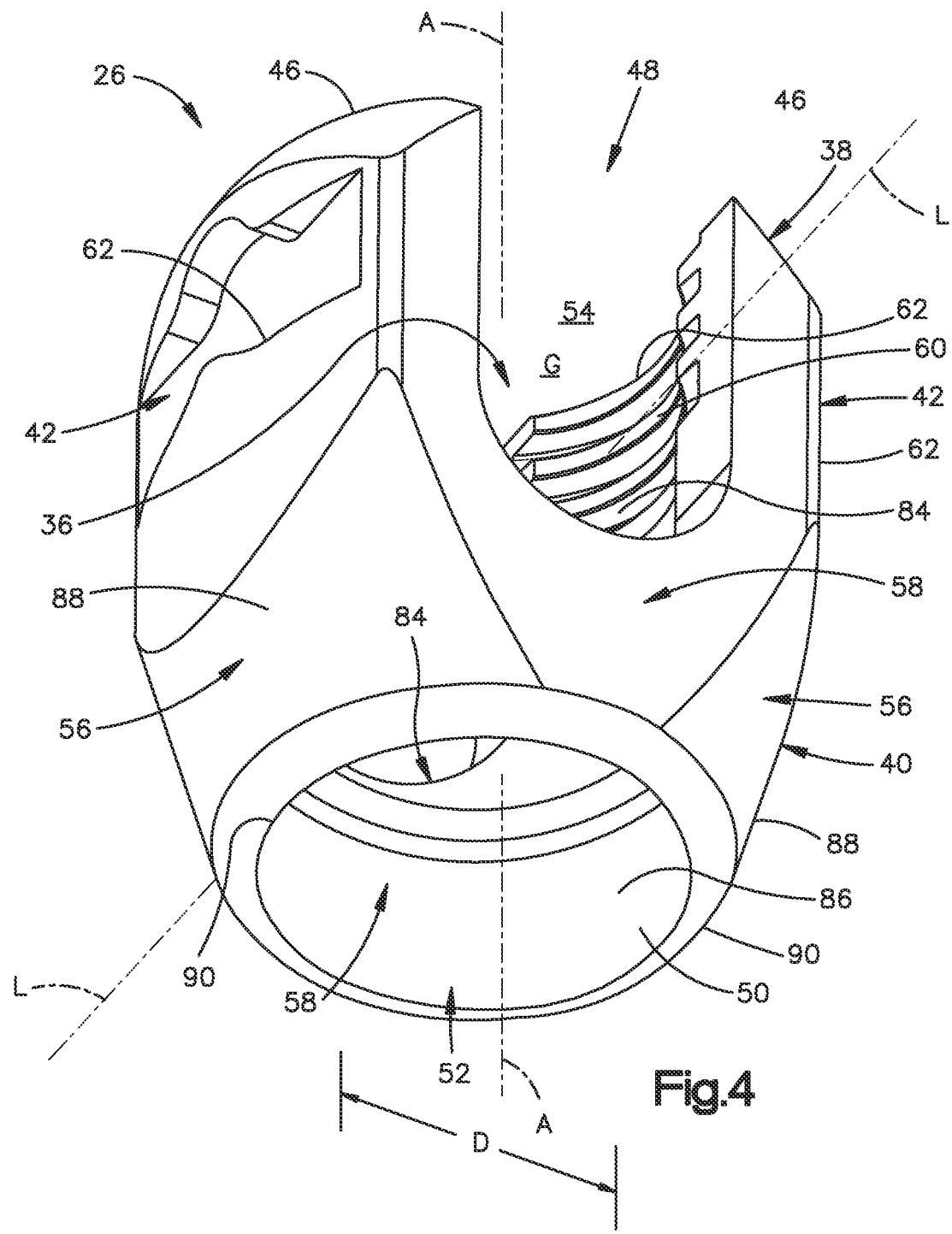
FIG. 4 is a perspective view of the anchor seat illustrated in FIG. 1B.

Referring now to FIG. 4, the anchor seat 26 includes an anchor seat body 38 that can be described as a generally cylindrical tubular body extending centrally along an axial axis A that extends generally in the anterior-posterior direction when the bone fixation element is implanted in the underlying vertebra. The body 38 includes a base 40 and a pair of spaced opposing arms 42 extending out (up in illustrated the orientation) from the base 40. The arms 42 can be substantially identically or identically constructed. The arms 42 define corresponding upper ends 46 that are also the upper ends of the body 38, and define an upper opening 48. The base 40 defines a lower end 50 that is also the lower end of the body 38, and defines a lower opening 52. The body 38 defines an axial bore 54 extending from the lower opening 52 to the upper opening 48.

The body 38 includes opposing support walls 56 and a pair of spaced opposing spacer walls 58 connected between the support walls 56. The support walls 56 can be substantially identically or identically constructed, and the spacer walls 58 can likewise be substantially identically or identically constructed. The arms 42 extend up from respective support walls 56, and can be shaped as desired. As illustrated, the arms 42 are arc-shaped with the axis of the arc passing through the plane of symmetry that bisects the anchor seat 26. Each arm 42 extends circumferentially about its axis less than 180°, such as between 60° and 150°, for instance approximately 90°. For instance, each arm 42 can extend circumferentially 90.5° about its axis.

Accordingly, a gap G extends circumferentially between adjacent circumferentially outer ends of the arms 42. The opposing gaps G are in alignment with the axial bore 54. The arms 42 can be disposed radially opposite each other such that the gaps G, in combination with the aligned portion of the axial bore 54, define a rod-receiving channel 36 that is sized and configured to receive the spine fixation rod 24 such that the spine fixation rod 24 extends through the bone fixation element 22. Thus, the gaps G are aligned in the longitudinal direction. The spine fixation rod 24 can thus extend through the opposing gaps G and the axial bore 54. The arms 42 define radially inner and outer surfaces 60 and 62, respectively. The inner surfaces 60 define threads 62, and are configured to threadedly receive the locking cap 34, as will now be described.

Figure 5C:
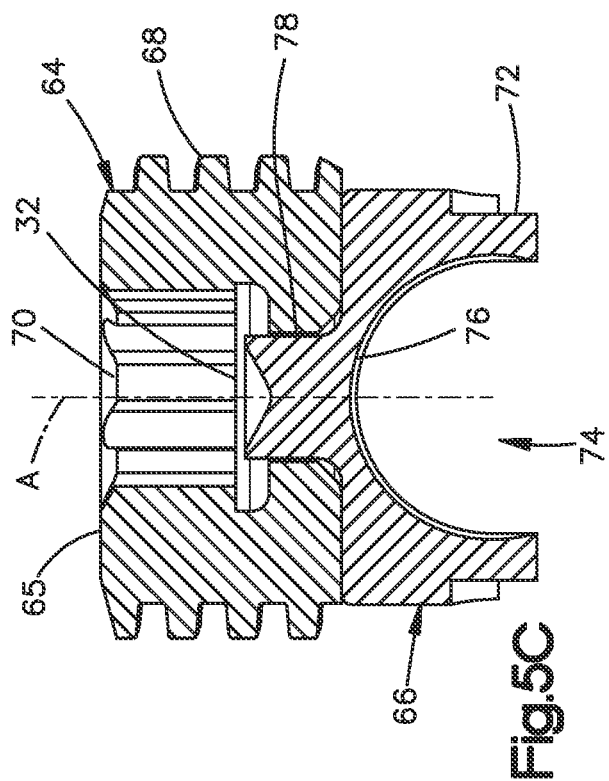
FIG. 5C is a sectional side elevation view of the locking cap illustrated in FIG. 5B.
Figure 5B:
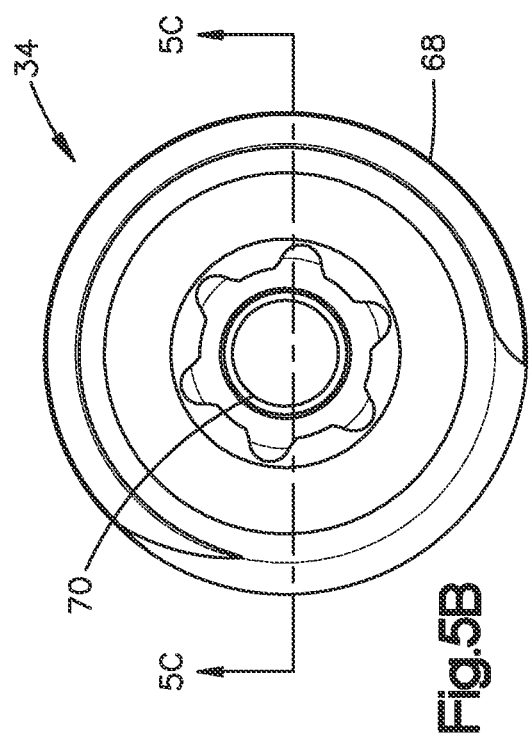
FIG. 5B is a top plan view of the locking cap illustrated in FIG. 5A.
Figure 5A:
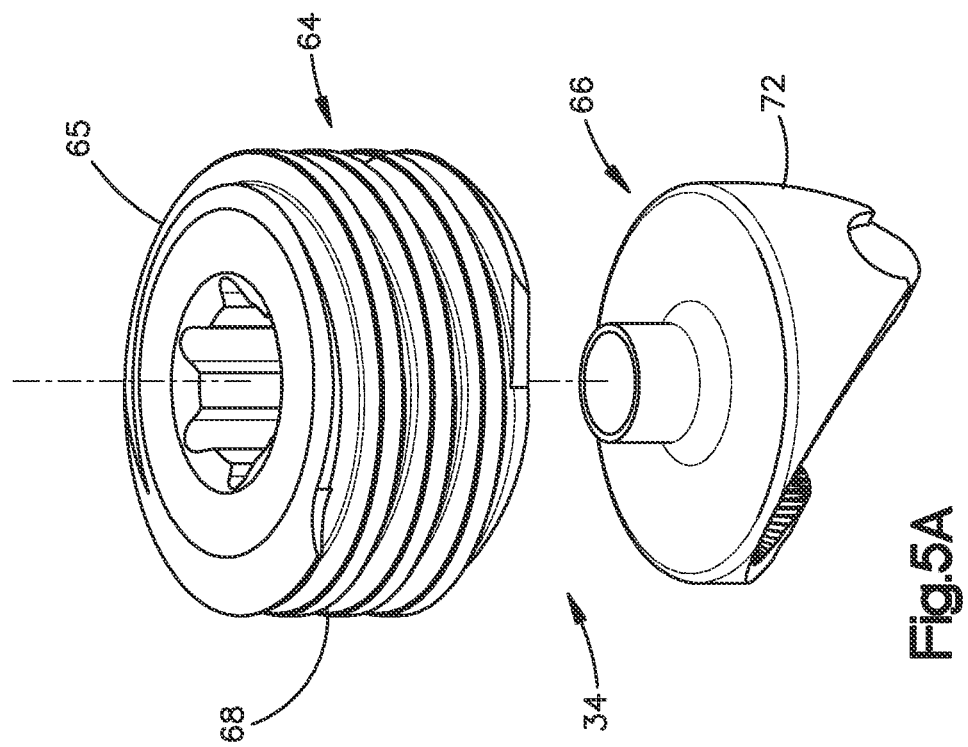
FIG. 5A is an exploded perspective view of the locking cap illustrated in FIG. 1B.

In particular, referring to FIGS. 5A-C, the locking cap 34 is illustrated as a set screw 64 and a saddle 66 operatively coupled to the set screw 64. The set screw 64 includes a generally cylindrical set screw body 65 having external threads 68 configured to threadedly engage the threads 62 formed on the inner surfaces 60 of the arms 42. In accordance with one embodiment, the threads 68 and 62 can incorporate inclined load flanks forming an angle with respect to the axis A of the bone fixation element 22. The load flanks may converge so that the top surface of the thread and the bottom surface of the thread converge. The angle may be between 0 degrees (0°) and 30 degrees (30°), and in one embodiment can be about five degrees (5°). One skilled in the art will appreciate that the threads may take on any alternative form as desired, including negative load threads, perpendicular threads, buttress threads, or the like.

The externally threaded set screw 64 generally provides flexibility when inserting the spine fixation rod 24 into the anchor seat body 38 such that the spine fixation rod 24 need not be completely reduced or seated within the body 38 prior to engagement of the locking cap 34. The set screw 64 is configured to be tightened within the anchor seat 26 against the spine fixation rod 24. The locking cap 34 may be constructed as desired for this purpose including, but not limited to, an externally threaded cap, a quarter-turn or partial-turn locking cap, a two-piece screw set, or the like.

The set screw 64 is illustrated as including a drive surface 70 provided as an internal recess extending vertically down into the upper end of the screw 64. The drive surface has any suitable shape configured to cooperate with a corresponding drive tool for threadedly securing the set screw 64 onto the anchor seat body 38. The drive surface 70 can define any shape as desired, for instance an external hexagon, a star drive pattern, a Phillips head pattern, a slot for a screw driver, a threading for a correspondingly threaded post, or the like.

With continuing reference to FIGS. 5A-C, the saddle 66 includes a saddle body 72 having a transverse recess 74 extending up into the bottom end of the saddle body 72. The recess 74 can define a round surface that extends about a longitudinally extending axis, such that the recess 74 is configured to receive the spine fixation rod 24 at a rod-contacting surface 76. The rod-contacting surface 76 can include a desired surface finish that adds roughness, such as, for example, a knurl, bead blasting, grooves, or other textured finish that increases surface roughness and enhances rod push through strength.

The saddle 66 can be coupled to the set screw 64 in any desired manner, including adhesion, mechanical fastening, and the like. In the illustrated embodiment, the saddle 66 includes a stem 78 extending centrally upward from the saddle body 72. The stem 78 is configured to be received in a central bore 32 extending vertically into the lower end of the set screw body 65, and can be fastened within the central bore with a rivet 80 or other like fastener. Accordingly, the saddle 66 is rotatable relative to the set screw 64, such that the saddle 66 can self-align with the spine fixation rod 24 as the set screw 64 is being rotated with respect to the anchor seat 26, for instance when the locking cap 34 is being tightened against the spine fixation rod 24.

Referring again to FIG. 4, and as described above, the anchor seat body 38 includes a pair of spaced opposing support walls 56 and a pair of spaced opposing spacer walls 58 connected between the support walls 56. The arms 42 extend up from respective support walls 56, such that the spacer walls 58 are disposed between the arms 42. Each of the spacer walls 58 defines opposing upper ends 84 and lower ends 82 that can be shaped as desired. The upper ends 84 are round in accordance with the illustrated embodiment, such that the upper ends 84 and the circumferentially outer ends of the arms 42 are adjoined to generally define a U-shape from a horizontal view through the gaps G. Thus, the upper ends 84 define the lower end of the gaps G.

The upper ends 84 can be shaped to conform generally with the outer surface of the spine fixation rod 24, such that the upper ends 84 receive and engage the spine fixation rod 24 during use. Alternatively, the upper ends 84 can be spaced slightly below the upper surface of the collet 28, such that the collet 28 supports the spine fixation rod 24 during use, as will be described in more detail below.

The support walls 56 each define opposing inner and outer surfaces 86 and 88, respectively. The support walls 56 and the spacer walls 58 flare inward toward the central axis A in a downward direction from the arms 42, and terminate at respective lower ends 90. The inner surfaces 86 of the opposing support walls 56 and spacer walls 58 at the lower end 90 define a distance D therebetween that is less than the distance between opposing radially opposing inner surfaces 60 of the arms 42. The distance D can be less than or greater than the diameter of the head 33 of the bone anchor 30. The inner surfaces 86 flare radially inward toward the central axis A, and toward each other, along a downward direction, and are each connected to bottommost, and innermost, surfaces that define respective abutment walls 92.

Referring also to FIGS. 4B and 7A, each abutment wall 92 defines respective inner abutment surfaces 93 that in turn define a distance therebetween that is substantially equal to the diameter of the neck 35, such that the abutment walls 92 are configured to abut opposing abutment surfaces of the bone anchor, which are illustrated as opposing sides of the outer neck surface 37 when the bone anchor 30 is disposed in the anchor seat 26. Thus, the abutment walls 92 can prevent or limit pivoting of the bone anchor 30 relative to the anchor seat 26 in a desired plane.

Figure 6:
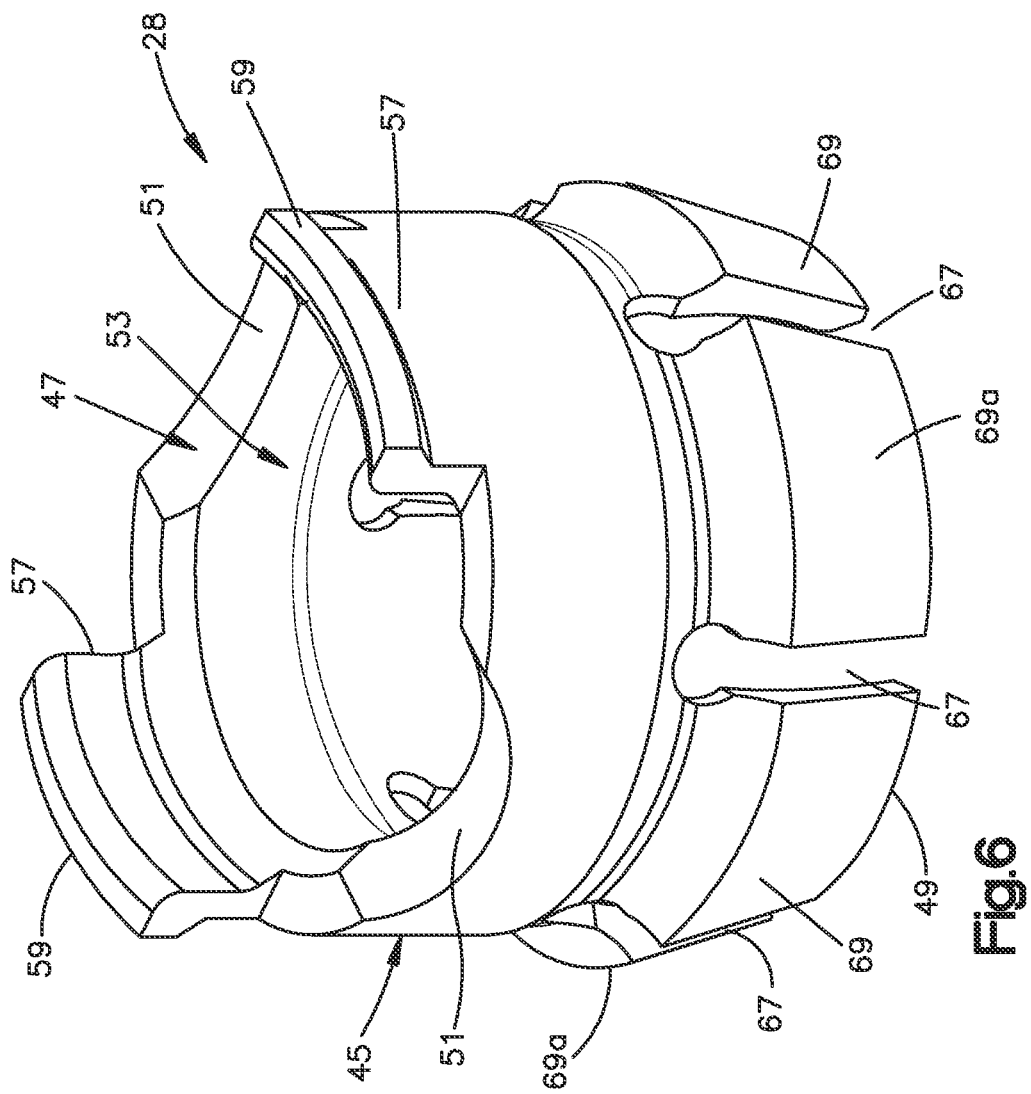
FIG. 6 is a perspective view of the collet illustrated in FIG. 1B.

Referring now to FIG. 6, the collet 28 includes a collet body 45 that defines a first or upper end 47 sized and configured to contact or support at least a portion of the spine fixation rod 24 when the rod is received within the rod-receiving channel 36, and a second or lower end 49 sized and configured to contact or otherwise engage, directly or indirectly, a portion of the bone anchor head 33. The collet body 45 is annular, and thus defines an axial bore 53 extending between and through the upper and lower ends 47 and 49. The axial bore 53 is aligned with the axial bore 54 when the collet 28 is installed in the anchor seat 26.

Referring to FIGS. 6 and 7A-B, the upper end 47 defines radially opposing upwardly facing seat portions 51 having a curvature or semi-spherical shape corresponding to the outer surface of the spine fixation rod 24, and is therefore configured to receive or otherwise support at least a portion (e.g., a lower portion) of the rod 24. The lower end 49 defines an inner surface 55 defining a curvature or semi-spherical shape corresponding to the outer surface of the anchor head 33, and is therefore configured to receive or otherwise engage at least a portion of the head 33, so that the head can rotate with respect to the collet 28 and the anchor seat 26, and can further pivot with respect to the collet 28 as permitted by the anchor seat 26. Because the bone anchor 30 can freely rotate about its axis of rotation B relative to the anchor seat 26, and thus the anchor seat 26 can likewise rotate about the bone anchor 30, the rod-receiving channel 36 can be aligned with the spine fixation rod 24 without advancing or withdrawing the bone anchor 30 in or out of the underlying bone. Thus, the bone anchor 30 can maintain a constant insertion depth in the underlying bone (e.g., vertebra 27) while adjusting the orientation of the rod-receiving channel 36.

Figure 8A:
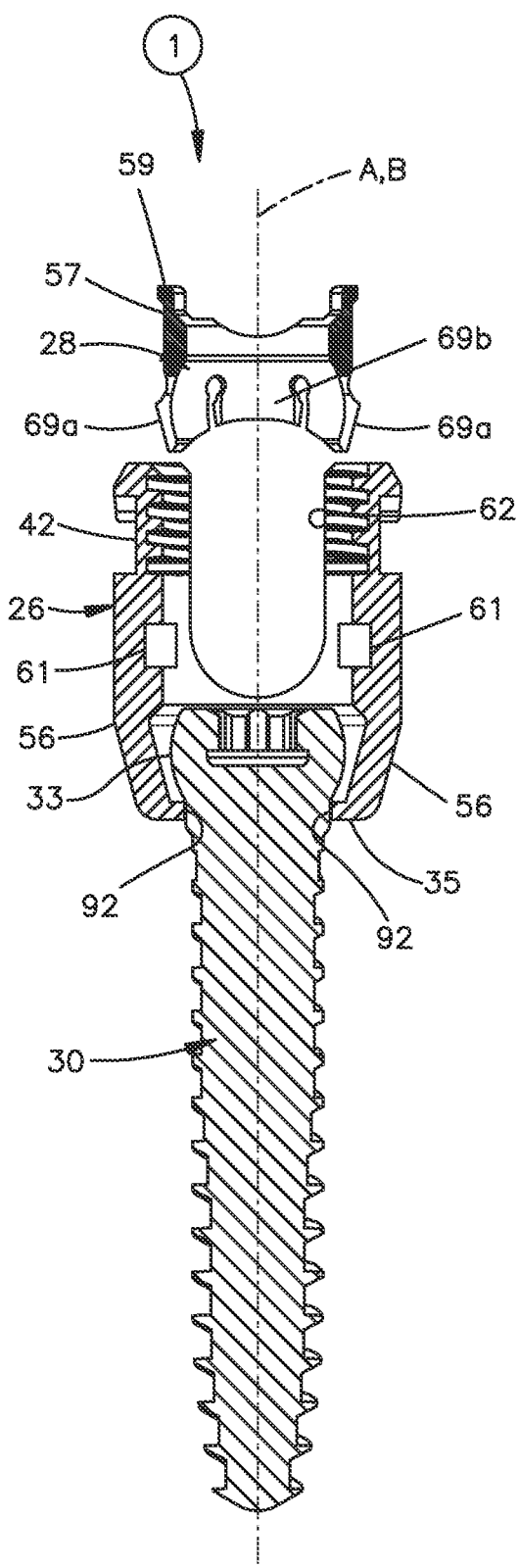
FIGS. 8A-D are schematic views illustrating a method for assembling the bone fixation element illustrated in FIG. 1A.
Figure 8B:
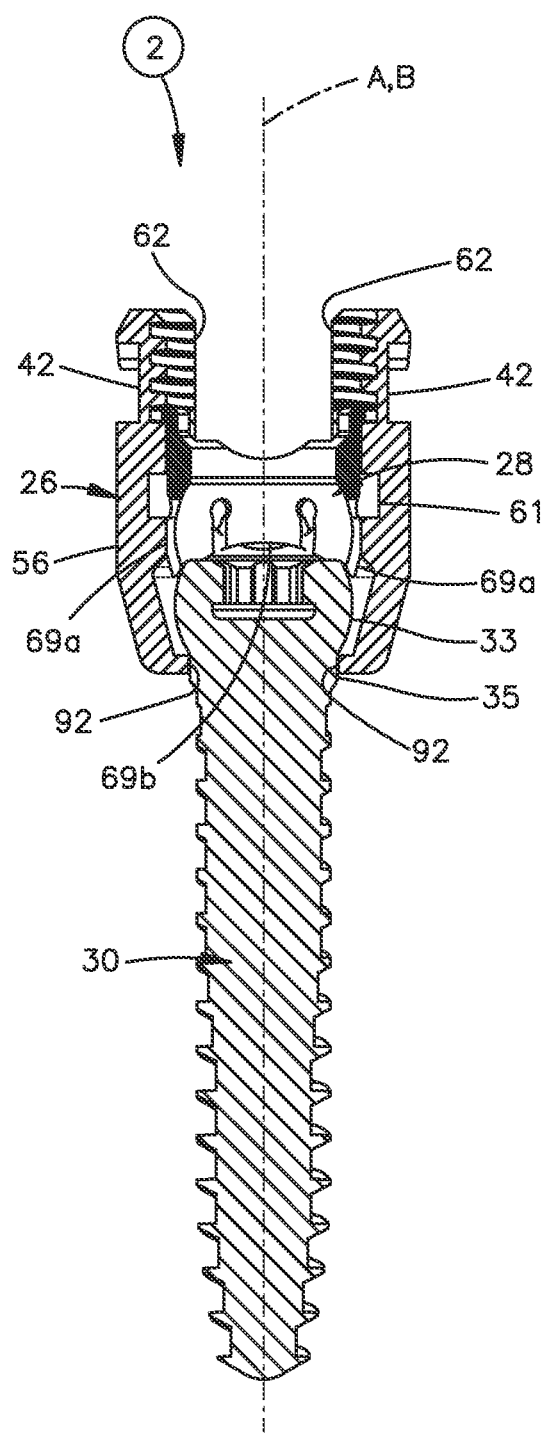
Figure 8C:
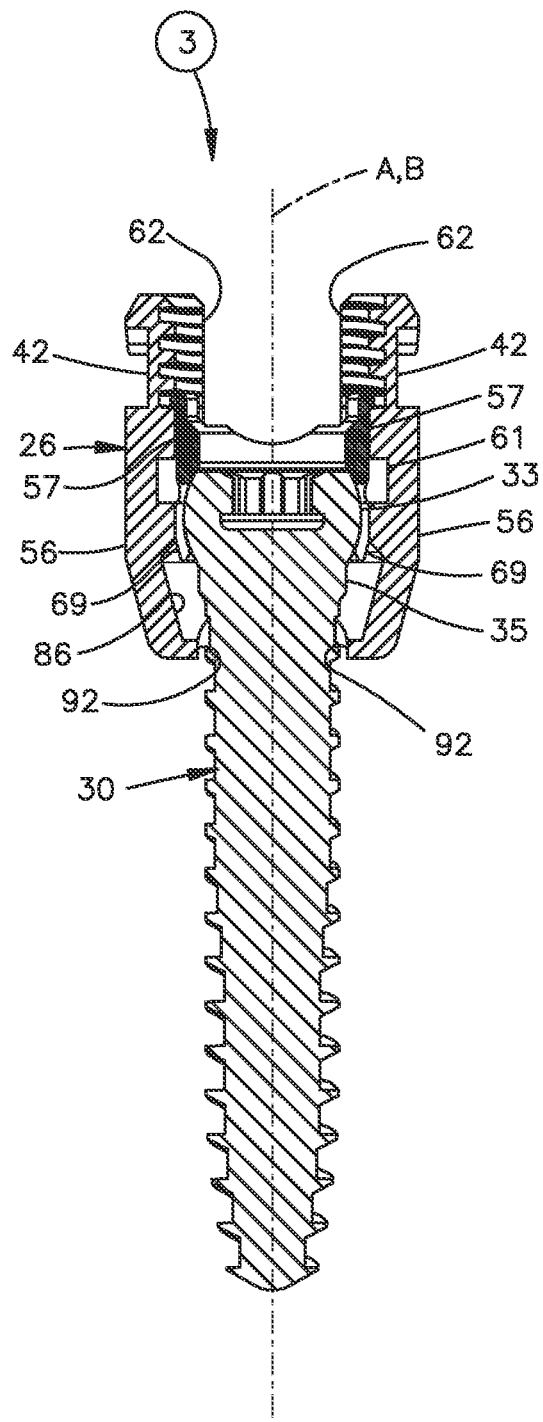
Figure 8D:
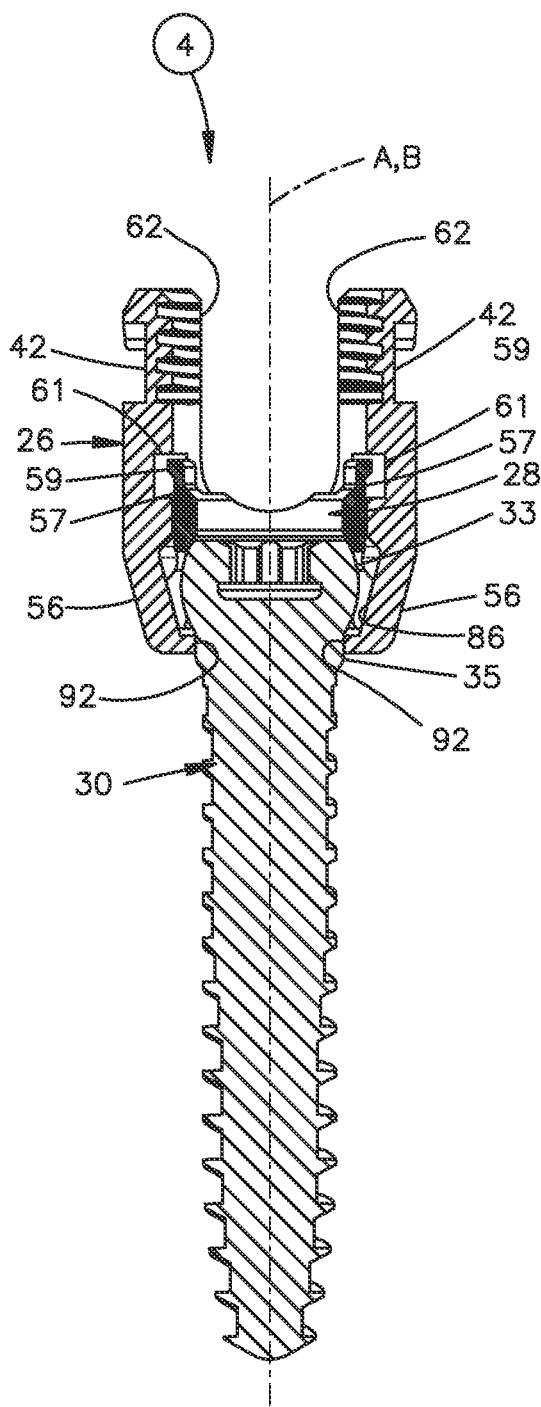

The collet 28 further includes a pair of flanges 57 extending up from the upper end 47 of the collet body 45 at a location radially between the seat portions 51. A locking lip 59 extends radially out from each flange 57. As best shown in FIG. 7A, the anchor seat 26 defines a pair of opposing recesses 61 (see FIG. 8A) formed radially in the opposing inner surfaces 86 of the support walls 56 at a location below the threaded inner surfaces 60 of the arms 42. During operation, the collet 28 can be inserted down into the anchor seat 26, thereby causing the flanges 57 to flex inwardly past the threaded inner surfaces 60, until the lips 59 clear the upper ends of the recesses 61, at which point the flanges 57 snap back out so that the lips 59 are disposed in the recesses 61. Interference between the lips 59 and the upper ends of the recesses 61 prevent the collet 28 from backing out through the upper end of the anchor seat 26. The recesses 61 further define a circumferential length substantially equal to that of the flanges 57 and locking lips 59, such that the collet 28 is rotationally fixed with respect to the anchor seat 26 in a position whereby the upper surface 47 is aligned with the spine fixation rod 24 when the spine fixation rod 24 is inserted into the anchor seat 26.

The lower end 49 of the collet 28 defines an outer diameter that is greater than the inner distance between the abutment walls 92. Accordingly, the collet 28 is unable to pass axially down through the lower end of the anchor body 26. The lower end 49 includes one or more slots 67 (illustrated as a plurality of slots) extending radially therethrough so as to define opposing pluralities of fingers 69 that are configured to pop over the head 33 of the bone anchor 30. When the collet 28 is disposed in the anchor seat 26 such that the lips 59 are disposed in the respective recesses 61, the fingers 69 are axially aligned with the abutment walls 92. Thus, as shown in FIGS. 7A-B, when the collet 28 and anchor 30 are installed in the anchor seat 24, the fingers 69 radially expand to conform to the outer surface of the anchor head 33 and the inner surfaces of the anchor seat 26. The inner diameters defined by the opposing fingers 69 are less than the outer diameter of the anchor head 33 to prevent the anchor 30 from being removed from the anchor seat 26 in an axially downward direction. The lower ends of the fingers 69 terminate at a location above the abutment walls 92. Accordingly, the fingers 69 do not interfere with the engagement between the anchor neck 35 and the abutment walls 92.

Referring now to FIGS. 8A-D, a method for assembling the vertebral implant 75 includes at step 1, inserting the bone anchor 30 vertically down through the axial bore 54, such that the shaft 31 extends through the lower opening 52 of the lower end 50 of the anchor seat 26, and the anchor head 33 is disposed above the abutment walls 92. This method step for inserting the bone anchor 30 into the anchor seat 26 can thus be referred to as top-end loading of the bone anchor 30 into the anchor seat 26. Next, at step 2, the collet 28 is inserted into the axial bore 54 to a location whereby the locking lips 59 can engage the lowermost threads 62 of the inner surface 60 of the arms 42. Next, at step 3, an upward force can be applied to the bone anchor 30 so as to insert the anchor head 33 into the lower end 49 of the collet 28. The locking lips 59 of the collet 28 brace against the anchor seat 26 inside the threads 62 to prevent the upward force applied by the screw 28 from causing the collet 28 to back out of the upper opening of the anchor seat 26. At step 4, a downward force is applied to the collet 28, thereby inserting the locking lips 59 into the recesses 61 in the manner described above, and locking the anchor 30 and collet 28 in the anchor seat 26.

During use, because the bone anchor 30 is rotatable with respect to the collet 28 and the anchor seat 26, a driving tool can engage the drive surface 39 of the head 33 so as to insert the threaded shaft 31 into the underlying bone, as shown in FIG. 1A. Next, as shown in FIGS. 8A-D, the anchor seat 26 can be rotated about axis A in the direction of Arrow R about the full 360° range of angles so as to align the rod-receiving channel 36 with the longitudinal axis of the spine fixation rod 24. Thus, the vertebral implant 75 can be referred to as a polyaxial vertebral implant, and the bone fixation elements 22 can be referred to as polyaxial bone fixation elements. Alternatively, it should be appreciated that the bone fixation element can allow the anchor seat 26 to rotate in one plane with respect to the axis A, and can thus be referred to as a monoaxial vertebral implant. It should be further appreciated that the vertebral implant can include a hook as the bone anchor 30 as opposed to a screw. Once the bone anchor 30 has reached a desired depth in the underlying vertebra, the spine fixation rod 24 can be inserted into the vertebral implant 75. In particular, the spine fixation rod 24 is inserted into the axial bore 54 either horizontally through the gaps G, or vertically down into the axial bore 54. It should be appreciated that the spine fixation rod 24 will be seated in the upper end 47 of the collet 28.

With continuing reference to FIGS. 8A-D, once the rod 24 is installed in the vertebral implant 75, the locking cap 34 can be attached to the assembly 75 so as to fully assemble the anchor assembly 22. In the illustrated embodiment, the external threads 68 of the set screw 64 are rotated within the inner threads 62 of the anchor seat arms 42, thereby causing the set screw and saddle 66 to move axially down in the axial bore 54. As the saddle 66 approaches the spine fixation rod 24, the saddle 66 is rotated with respect to the set screw 64 so as to bring the rod-contacting surface 76 into alignment with the spine fixation rod 24. Once the saddle 66 is aligned with the spine fixation rod 24, the set screw 64 is continuously threadedly inserted into the bone anchor 26, such that the locking cap 34 can be tightened against the rod 24, thereby applying a downward axial force to the rod 24. The locking cap 34 can be said to be in an initial position when installed in the locking cap 34 but before applying an axial force against the spine fixation rod 24. The axial force applied to the rod 24 by the locking cap 34 is transmitted to the collet 28, which causes the fingers 69 to ride along the inner surfaces 86 of the support walls 56 and spacer walls 58.

As the fingers 69 ride along the walls 56 and 58, they become radially inwardly displaced due to the inward flare of the inner surfaces of the walls 56 and 58, thereby radially biasing, or radially compressing, the fingers 69 against the anchor head 33. Increasing radial compression of the fingers 69 against the anchor head 33 causes frictional forces between the fingers 69 and the anchor head 33 that resist rotation of the anchor 30 about the axis A relative to the anchor seat 26, collet 28, and spine fixation rod 24. When the locking cap is fully tightened to a locked position, the resulting frictional forces prevent the anchor 30 from movement relative to the anchor seat 26, collet 28, and spine fixation rod 24. Thus, the locking cap 34 is configured to transmit a locking force onto the collet 28 and bone anchor 30 to fix or lock the position of the bone anchor 30 relative to the anchor seat 26 and spine fixation rod 24. It should thus be appreciated that the spine fixation rod 24 is thus implanted to the underlying vertebra that is engaged by the bone anchor 30.

It should be appreciated that the above-described method steps can be performed for each bone fixation element of the bone fixation assembly 20 as desired. Furthermore, it should be appreciated that the while the bone fixation elements 22a-d have been described as each including the vertebral implant 75 described above, the bone fixation elements 22a-d can include any alternatively constructed vertebral implant suitable for fixing the spine fixation rod 24 to the underlying vertebrae 27. For instance, the vertebral implant 75 can be constructed so as to permit the bone anchor 30 to be implanted into underlying bone before the anchor head 33 is inserted into the collet 28. In one embodiment, the abutment walls 92 are slotted so as to expand over the anchor head 33. Accordingly, the anchor seat 26 and collet 28 can be popped onto the head 33 from above instead of inserting the anchor 30 down through the anchor seat 26 in the manner described above. The method step of popping the anchor seat 26 over the head 33 can be referred to as bottom-end loading of the anchor 30 into the anchor seat 26. It should be further appreciated that while the bone fixation assembly 20, including the bone fixation elements 22 and vertebral implants 75, have been described in connection with one embodiment, the bone fixation assembly 20, including the bone fixation elements 22 and vertebral implants 75, can be constructed in accordance with any embodiment suitable to be implanted into a plurality of vertebrae and be connected by a spine fixation rod, such as described in U.S. patent application Ser. No. 11/603,428, filed Nov. 21, 2006, and published as U.S. Publication No. 2007/0118123, published on May 24, 2007, the disclosure of which is hereby incorporated by reference as if set forth in its entirety herein.

Figure 9:
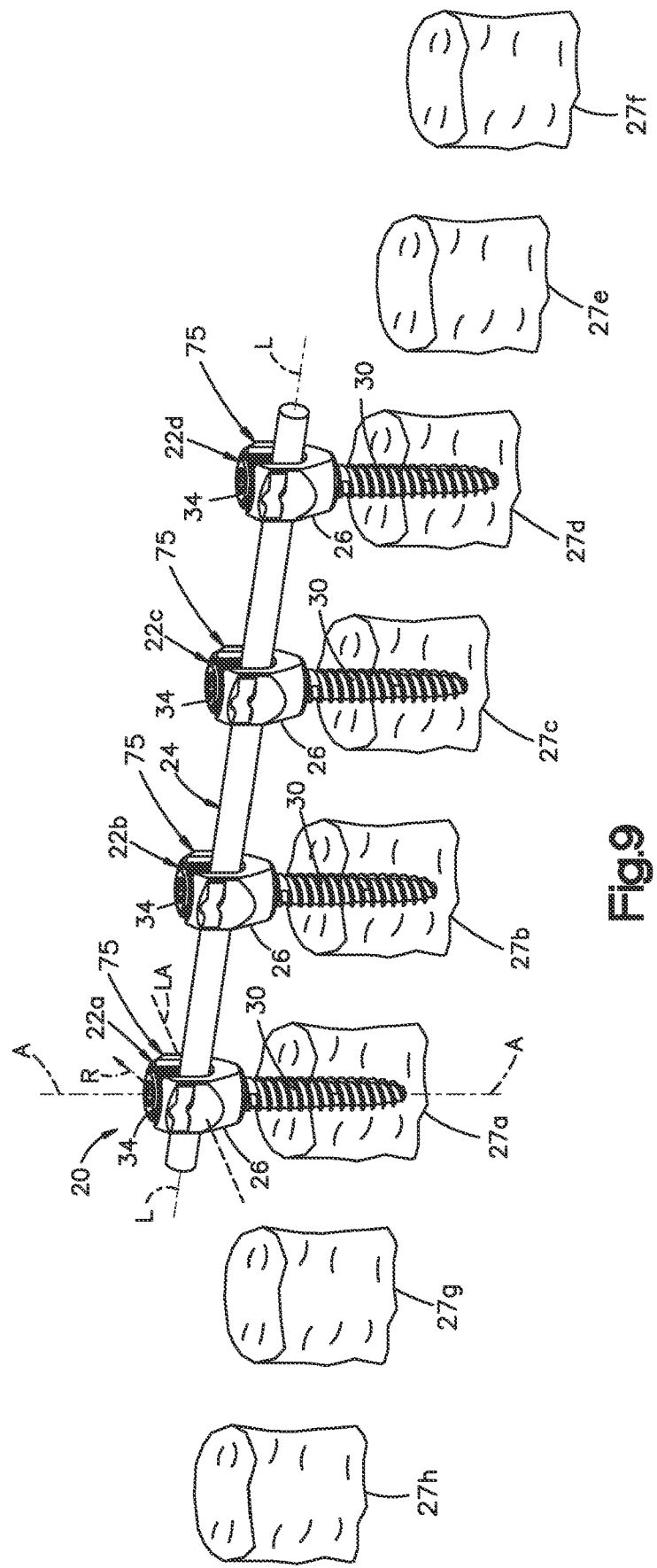
FIG. 9 is a perspective view similar to FIG. 1A, but showing a plurality of superior and inferior vertebrae with respect to the previously secured vertebrae.

Referring now to FIG. 9, it should be appreciated that the while the spine fixation rod 24 is implanted in a plurality of vertebrae 27a-d in the bone fixation assembly 20, it may become desirable at a future date to extend the bone fixation assembly 20 to affix at least one such as a plurality of vertebrae to the vertebrae 27a-d. For instance, it may be desirable to affix at least one such as a plurality of inferior vertebrae 27e-f to the vertebrae 27a-d. Alternatively or additionally, it may be desirable to affix at least one such as a plurality of superior vertebrae 27g-h to the vertebrae 27a-d. Thus, the spine fixation rod 24 can be referred to herein as a previously implanted spine fixation rod. As illustrated, the vertebra 27a is the cranial-most vertebra that is secured to the spine fixation rod 24, and the vertebra 27d is the caudal-most vertebra that is secured to the spine fixation rod 24. The vertebra 27h is superior to the vertebra 27a, and the vertebra 27g is superior to the vertebra 27h. The vertebra 27e is inferior to the vertebra 27d, and the vertebra 27*f* is inferior to the vertebra 27*e*. The vertebrae 27*g-h* and 27*e-f* can be referred to as new vertebrae.

Referring now to FIGS. 10A-D, an extender system 100 includes a top-loading polyaxial spinal construct extender 105 that is configured to be operatively coupled to the spine fixation rod 24 of a previously implanted bone fixation element 22 or newly implantable bone fixation element so as to join one or more vertebrae, that have been joined together using the bone fixation system 20, with an adjacent bone. Thus the polyaxial spinal construct extender 105 can be configured to extend the bone fixation system 20 to one or more adjacent spinal levels. One having ordinary skill in the art will appreciate that the polyaxial spinal construct extender 105 is not limited to extending a construct that has already been implanted and may be utilized in original spinal surgeries, potentially in a minimally invasive manner, to fix multiple levels of a patient's vertebrae.

The polyaxial construct extender 105 includes a polyaxial extension member 139 constructed as a rod 140 that having a substantially cylindrical rod body 141 that defines a proximal end 141*a* and an opposed distal end 141*b*. The polyaxial extender rod 104 includes an engagement member illustrated as a loop 142 that is attached to the proximal rod body end 141*a*, and an aperture 143 extending vertically through the loop 142. The distal end 141*b* can be coplanar with the loop 142 as illustrated. Alternatively, the distal end 141*b* can be angularly or otherwise vertically offset with respect to the loop 142. The polyaxial extender rod 140 further includes a bushing 150 disposed within the aperture 143, and secured to the loop 142. The extender 105 further includes a tapered fastener illustrated as a tapered set screw 130 configured to connect to both the bushing 150 and the anchor seat 26 (either of the previously implanted bone fixation system 20 or of a new bone fixation system), and a locking member illustrated as a locking nut 160 configured to lock the extender rod 104 to the set screw 130.

The tapered set screw 130 includes a proximal portion 130*a*, a distal portion 130*b*, and a middle portion 130*c* disposed between the proximal portion 130*a* and the distal portion 130*b*. The set screw 130 includes at the proximal portion 130*a* a non-tapered exterior surface having an exterior set of threading 131 that is configured to engage an interior set of threading on the locking nut 160. The distal portion 130*b* of the tapered set screw 130 includes a non-tapered exterior surface 132 having an exterior set of threading 133 that is configured to engage a set of interior threading of the anchor seat 26. The set screw 130 includes at the middle portion 130*c* a tapered nonthreaded exterior surface 134 that is configured to abut the interior surface 151 of the bushing 150. The tapered exterior surface 134 is configured such that the circumference of the middle portion 130*c* increases along a direction from the proximal portion 130*a* toward the distal portion 130*b*.

The bushing 150 includes a flat superior surface 152, a flat inferior surface 153, a central longitudinal axis 154 extending between the superior surface 152 and the inferior surface 153, and a partially spherical exterior surface 155 extending between the flat superior and inferior surfaces 152 and 153, and an interior surface 151 surrounding a hollow interior 156. The bushing 150 includes a split 157 extending along the longitudinal axis through the exterior and interior surfaces 155 and 151 to allow the bushing to expand in circumference as the tapered middle portion 130*c* of the tapered set screw 130 is driven into the interior 156.

The interior surface 151 of the bushing 150 includes an inferior taper 151*a* and a superior taper 151*b*, such that the inferior taper 151*a* extends between the inferior surface 153 and a mid-point of the interior surface 151, while the superior taper 151*b* extends between the superior surface 152 and the point of the interior surface 151. The point of the interior surface 151 is generally the circular line at which the two tapers meet to form an apex 158. The inferior taper 151*a* and the superior taper 151*b* each preferably define an angle with respect to the longitudinal axis 154 that matches the taper angle of the exterior surface 134 of the middle portion 130*c* of the tapered set screw 130.

The bushing 150 is press fit into the aperture 143 of the loop 142 of the extender rod 140. The partially spherical exterior surface of the bushing 150 is generally similar or identical to the spherical geometry of the interior surface of the loop 142, such that the bushing 150 is polyaxially rotatable within the aperture 143 in an initial state prior to insertion of the screw 130. Once the screw 130 is inserted into the bushing 150, the tapered exterior surface 134 of the screw 130 rides along the interior surface 151 of the bushing, can causes the split 157 to expand, such that the exterior surface 155 of the busing is pressed against the interior surface loop 142, thereby locking the position of the bushing 150 inside the loop 142.

Referring now also again to FIG. 9, the system 100 can also include a newly implanted bone fixation element 22*g* disposed at an adjacent vertebra, for instance the superior vertebra 27*g* as illustrated, or the inferior vertebra 27*e*. The polyaxial extender rod 140 provides the spinal fixation rod that extends through the anchor seat 26 of the newly implanted bone fixation element 22*g*. Thus, the polyaxial extender rod 140 is coupled between the newly implanted bone fixation element 22*g* and another bone fixation element 22*a*, which can be part of a previously implanted bone fixation assembly 20.

Thus, during operation, the top loading polyaxial construct extender 105 may be implemented to extend a previously implanted spinal construct or bone fixation assembly 20 that includes the previously implanted bone fixation element 22*a* to an adjacent bone, illustrated as an adjacent spinal level, and create a rigid connection therebetween during revision surgery. An incision is made at the spinal level adjacent to, for example adjacent to the most cranial (or most caudal), level of an existing spinal construct in need of revision. The incision is made over the outermost preexisting bone fixation element 20 and the new vertebrae to be fixed, and an incision need not be made across the other vertebrae 27*a*-27*d* of the preexisting bone fixation element 20 because the preexisting spine fixation rod 24 is not removed. The new bone fixation element 22*g*, with the exception of the locking cap 34, is implanted into the adjacent spinal level 27*g*. Otherwise stated, the vertebral implant 75 of the new bone fixation element 22*g* is implanted into the adjacent spinal level 27*g*. Through the same incision, or using a second incision, the locking cap 34 is removed from an outermost, such as the cranial most, bone fixation element 22*a* (or caudal most bone fixation element 22*d*).

The tapered set screw 130 is then coupled to the previously implanted bone fixation element 22*a* by screwing the threading 133 at the distal end 130*b* of the tapered set screw 130 into the threading on the interior of the anchor seat 26. Because the locking cap 34 of the previously implanted vertebral implant 22*a* has been removed, it can also be said that the tapered set screw 130 is coupled to the polyaxial vertebral implant 75 of the previously implanted bone fixation element 22*a*. The extender rod 140 is then connected between the previously implanted polyaxial vertebral implant 22*a* and the newly implanted vertebral implant 22*g* by placing the bushing 150 retained within the loop 142 around the middle portion of the tapered set screw 130 and the opposite end of the extender rod 140 vertically down into the anchor seat 26 of the newly implanted bone fixation element 22g. The spherical exterior surface 155 of the bushing 150 and complementary spherical interior surface 147 of the loop 142 that defines the aperture 143 allows the bushing 150 to rotate polyaxially within the aperture 143 of the loop 142. The doubly tapered interior surface 151 of the bushing 150 allows orientational freedom in coupling the extender rod 140 to the tapered set screw 130, because the oppositely oriented tapers allow the extender rod 140 to be coupled to the tapered set screw 130 in either direction, such that there is no incorrect orientation.

Figure 10C:
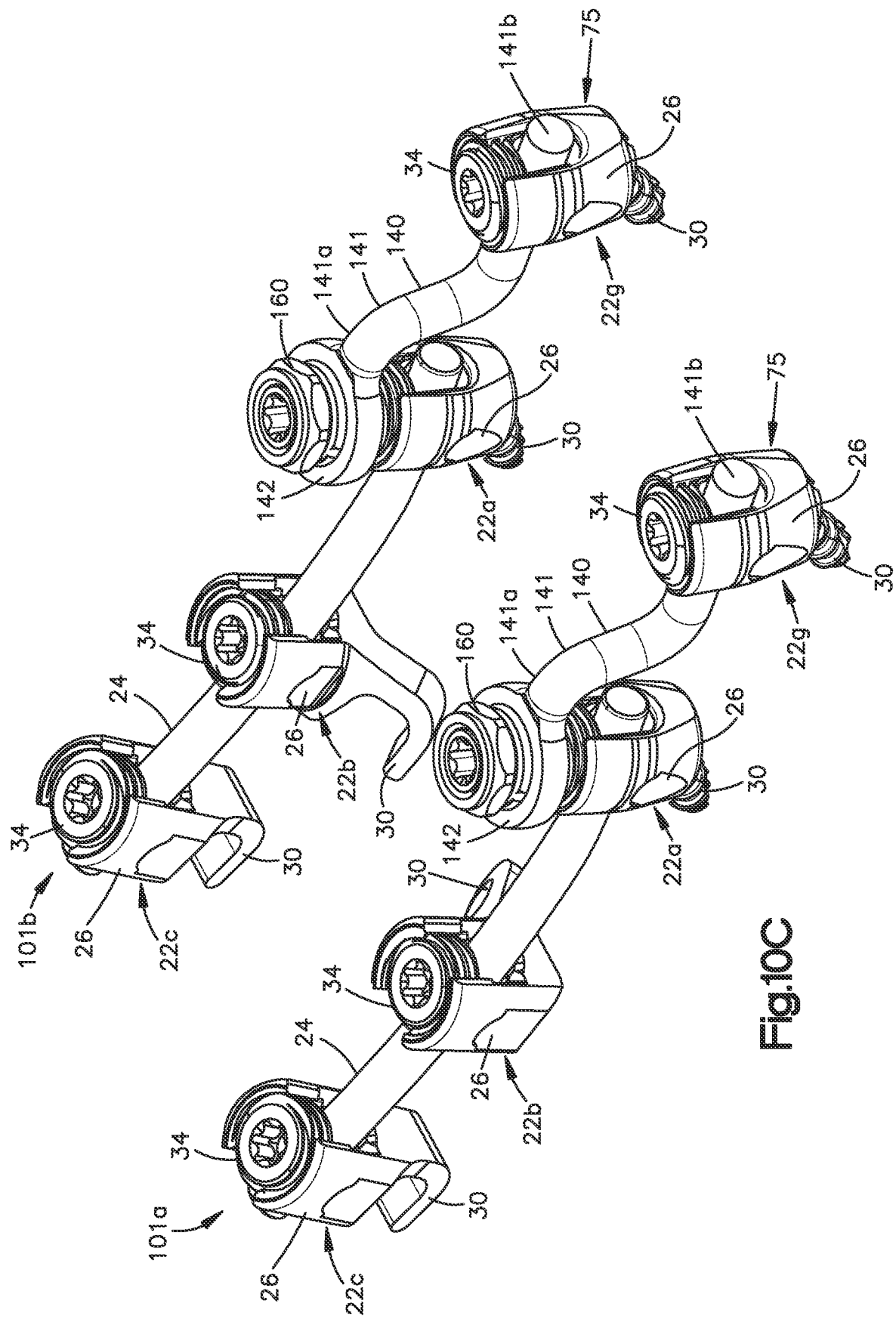
FIG. 10C is a perspective view of the extender system illustrated in FIG. 10A coupled to a previously implanted bone fixation assembly.
Figure 10D:
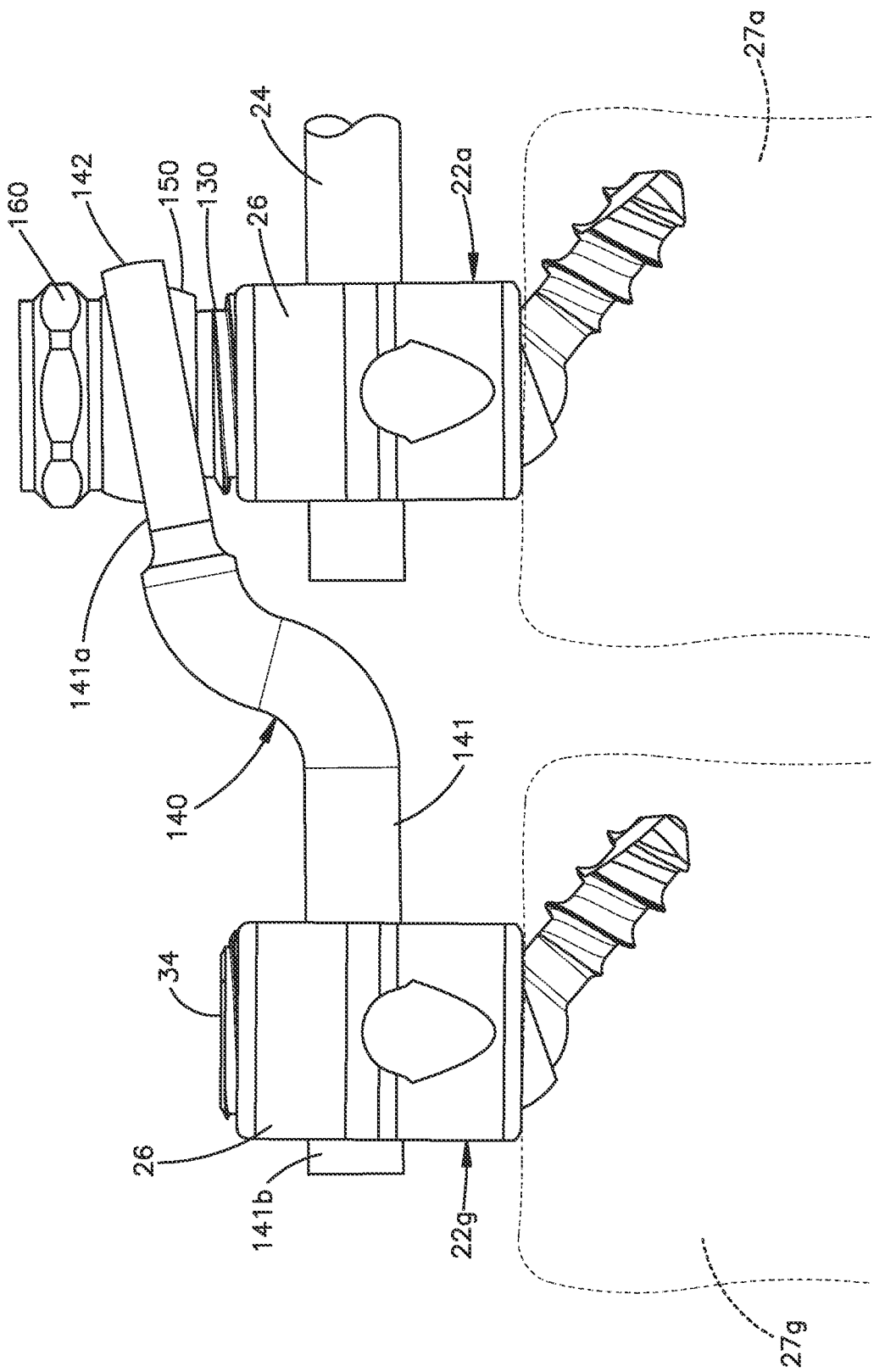
FIG. 10D is an enlarged side elevation view of a portion of the extender system illustrated in FIG. 10A coupled to a previously implanted bone fixation assembly.
Figure 14C:
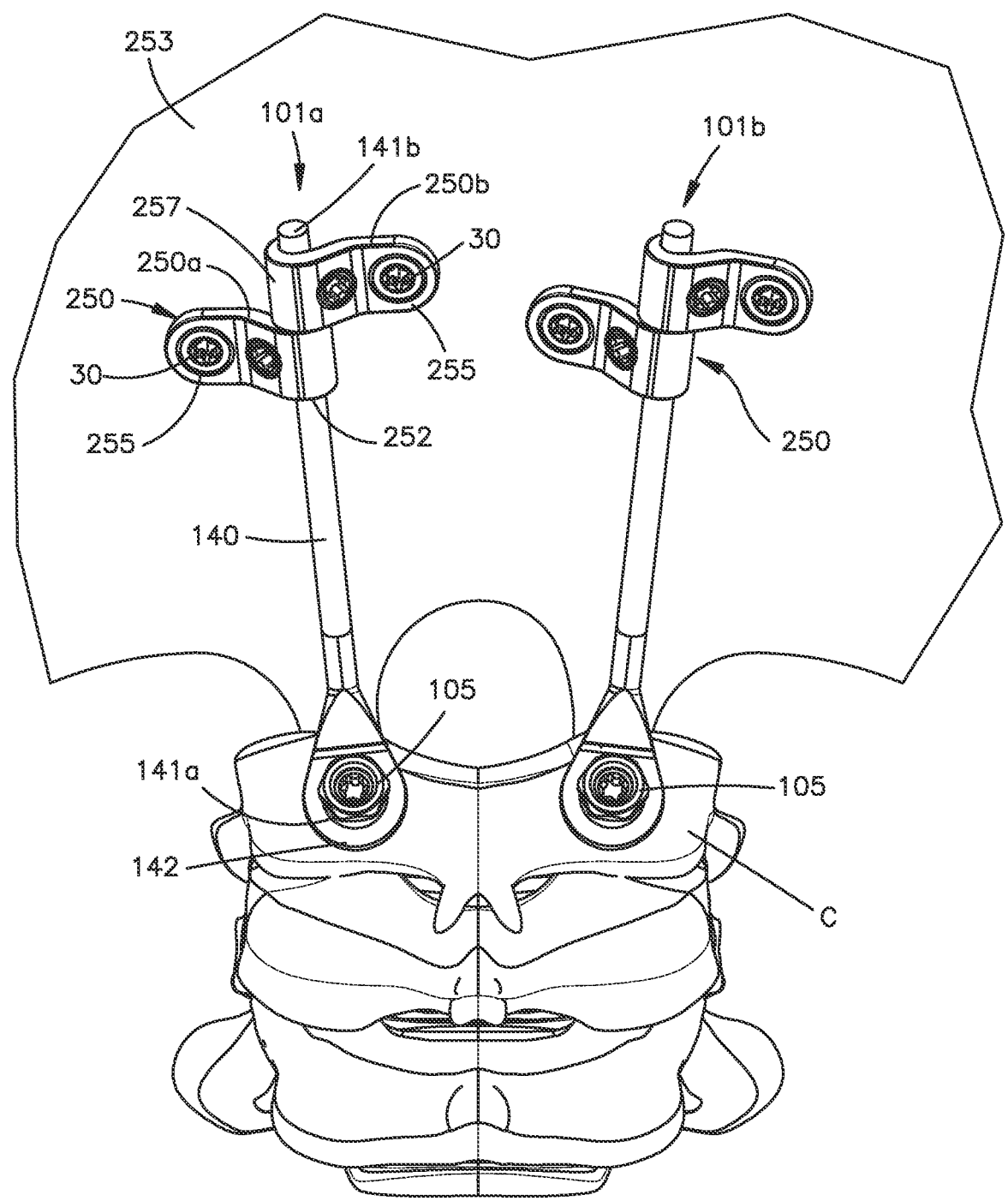
FIG. 14C is a perspective view of the extender systems illustrated in FIG. 14A connected between an occiput and a spine.
Figure 14D:
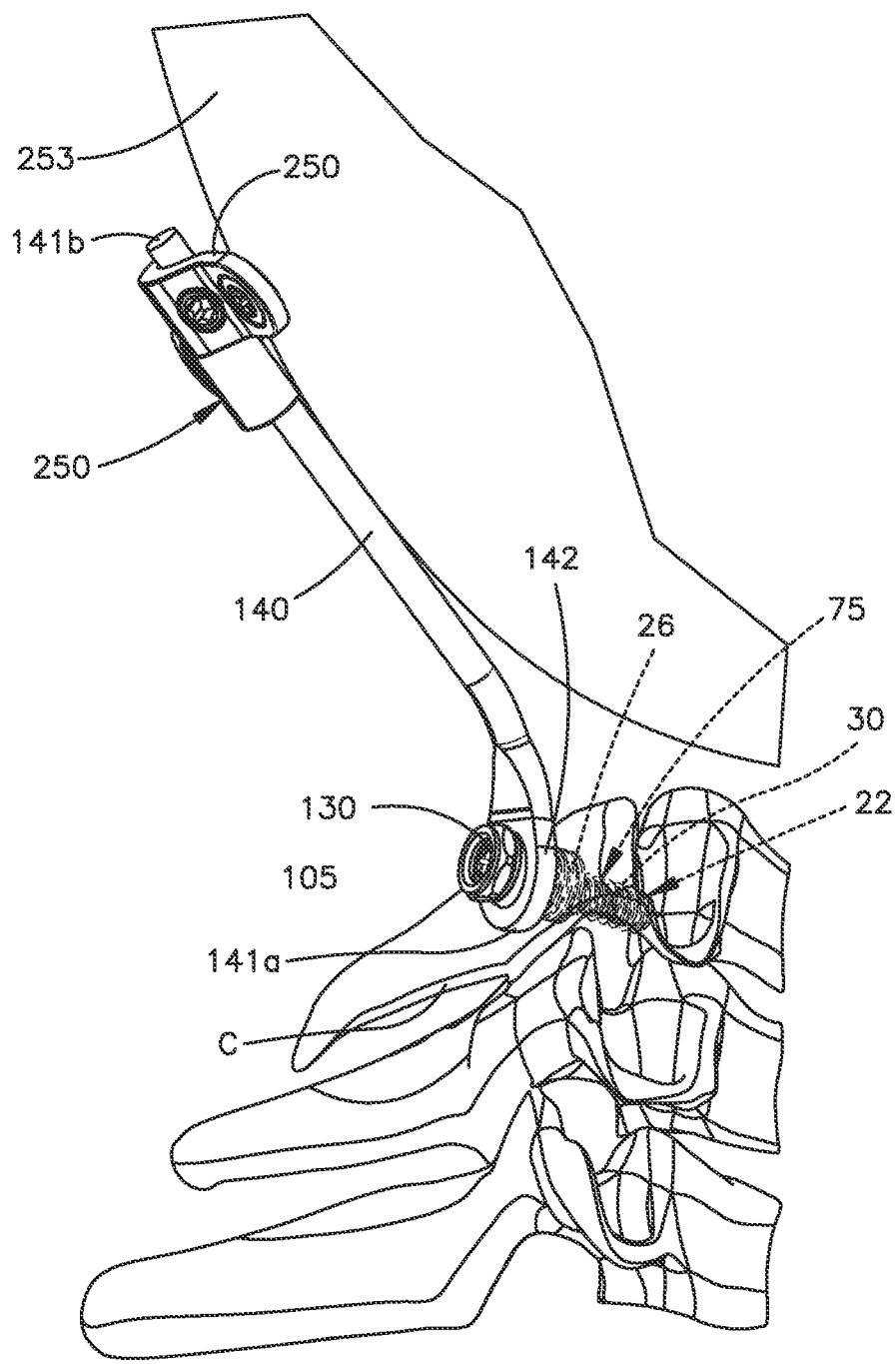
FIG. 14D is another perspective view of one of the implanted extender systems illustrated in FIG. 14C.

The locking nut 160 is then screwed down, e.g., by engaging an instrument-engaging feature on the exterior or superior surface of the locking nut 160, over the proximal or superior portion 130a of the tapered set screw 130, forcing the extender rod 140 and the bushing 150 to advance distally with respect to the middle portion 130b of the tapered set screw 130 and, in so doing, forcing the bushing 150 to expand and match tapers of the interior surface 151 and the exterior surface 134 of the middle portion 130c of the tapered set screw 130 to lock via an interference fit. The locking cap 34 is then screwed into the top of the anchor seat 26 until the angular orientation of the bone anchor 30 is locked with respect to the anchor seat 26 and the extender rod 140 is secured in the bone fixation element 22. As illustrated in FIG. 10D, the extender rod body 141 can be substantially "s-shaped", such that the proximal end 141a is disposed posterior with respect to the distal end 141b. Alternatively, the extender rod 140 can be substantially linear, or define a substantially constant or variable curvature (see FIGS. 14A-C), and the bushing 150 can be oriented such that the proximal end 141a is disposed posterior with respect to the distal end 141b. Thus, the proximal end 141a can be installed above the pre-existing spine fixation rod 24, while the distal end 141b can be substantially aligned with the pre-existing spine fixation rod 24. In the case of the system 100 including parallel rows 101a and 101b of fixation elements 22 and spinal construct extenders 105, the above-described fixation procedure is repeated for the opposite row.

To extend a previously implanted bone fixation assembly 20 caudally, as opposed to cranially, the top-loading polyaxial spinal construct extender 105 is connected to the vertebral implant 75 of the inferior bone fixation element 22d in the manner described above, a new bone fixation element is secured in an inferior vertebra, such as vertebra 27e, and the extender rod 140 is connected between the vertebral implant 75 of the inferior most pre-existing fixation element 22 and the newly implanted bone fixation element in the manner described above.

The top-loading capability of the system 100 enables less invasive, less difficult, and less time consuming revision surgeries to occur when compared to conventional spinal revision surgery systems and methods that generally necessitate the entire previously implanted spinal construct to be disassembled and then reassembled with a longer rod using another large incision with the potential for significant blood loss in order to fuse an adjacent spinal level. The system 100 generally reduces the necessary incision length and decreases surgical time, blood loss, postoperative pain, and healing time. Further, the system 100 of the first preferred embodiment may enable minimally invasive techniques to be utilized when constructing a multiple level spinal rod assembly as the relatively short length of the extender rod 140 permits insertion of multiple fixation screws and extender rods 140 into a single small incision, sequential stacking of the rods across multiple levels and relatively easy manipulation of the extender rods 140 into engagement with the fixation screws.

It should be appreciated that the rod 140 can include a dampening mechanism so as to provide additional motion as desired, for instance between one portion of the rod 140 and the loop 142. In addition, the rod 140 can be entirely made of an elastic material further providing a dynamic connection between levels. For example, the rod body 141 and/or the loop 142 can be constructed of a polyetheretherketone (PEEK) material that permits damping or limited motion between adjacent polyaxial vertebral implants 75. The loop 142, rod 140, bushing 150, locking nut 160, set screw 130, spinal rod 42, anchor seat 26, and/or other components of the system 100 can be configured to limit the ultimate movement of the components relative to each other to prevent over-extension or over-compression of the components relative to each other even if certain of the components are constructed to permit motion or to be dynamic.

Figure 11A:
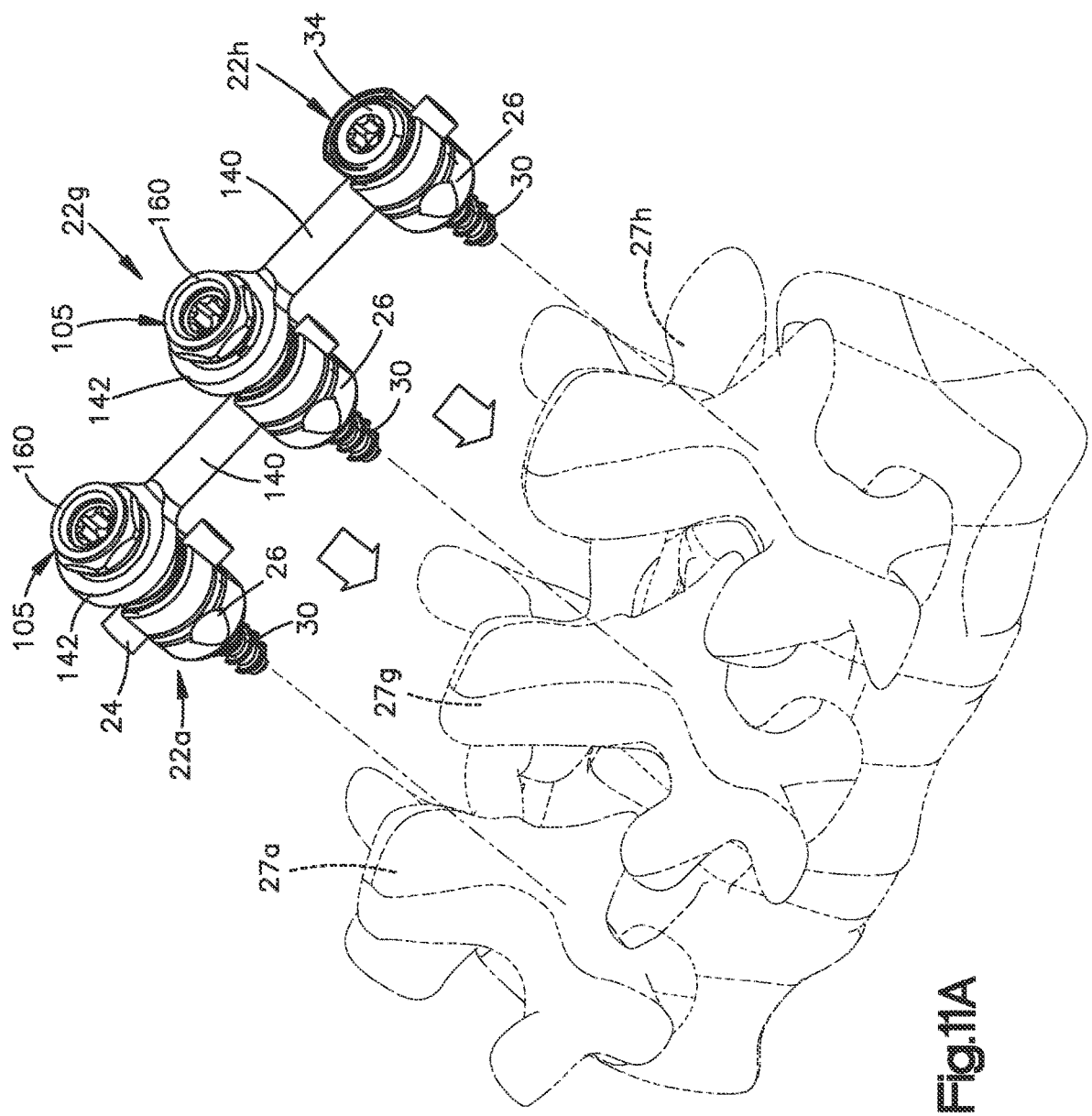
FIG. 11A is an exploded view of a cascading extender system to be implanted into a plurality of vertebrae.
Figure 11B:
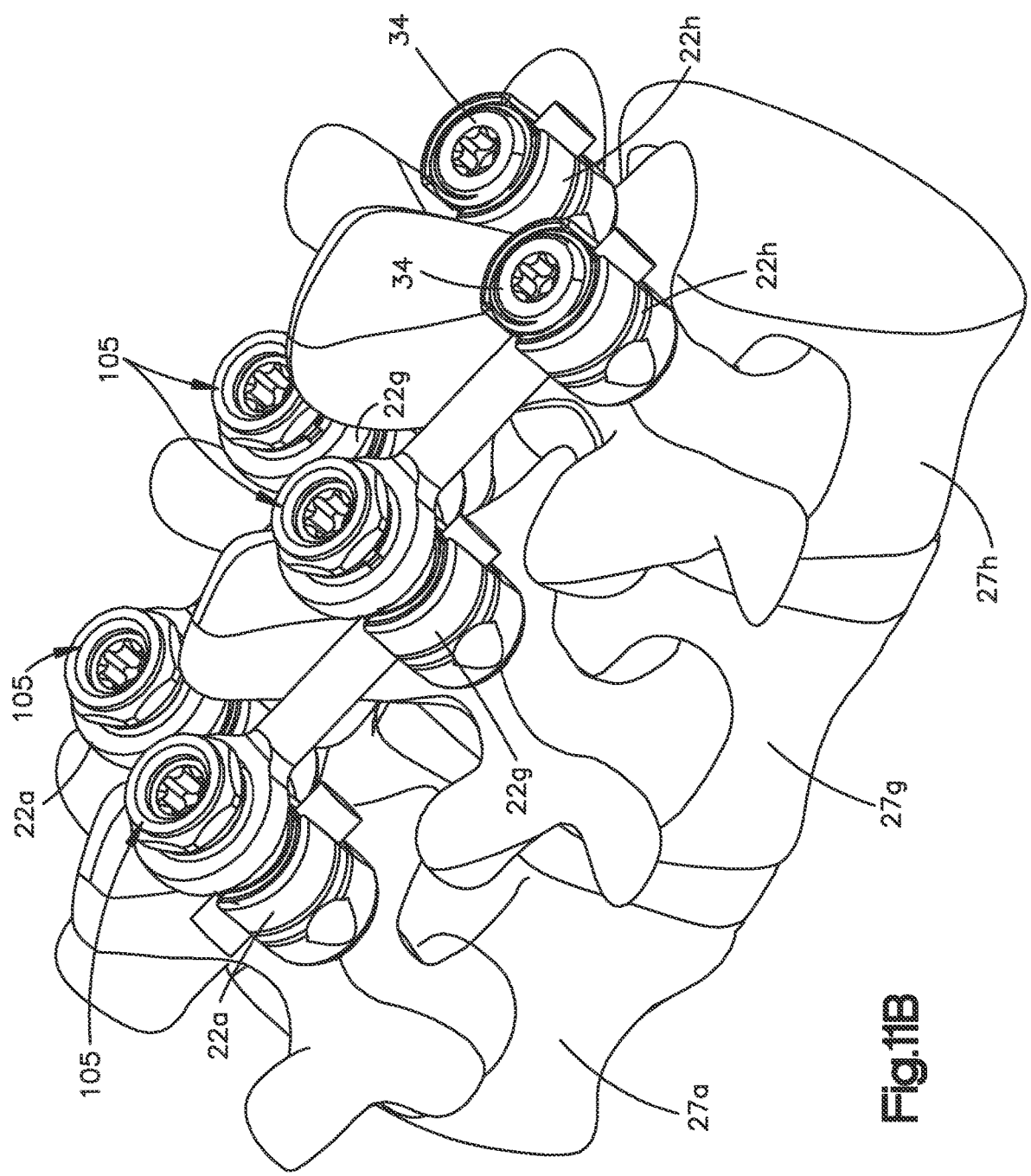
FIG. 11B is a perspective view of a pair of rows of the cascading extender system illustrated in FIG. 11A implanted into the vertebrae.
Figure 11C:
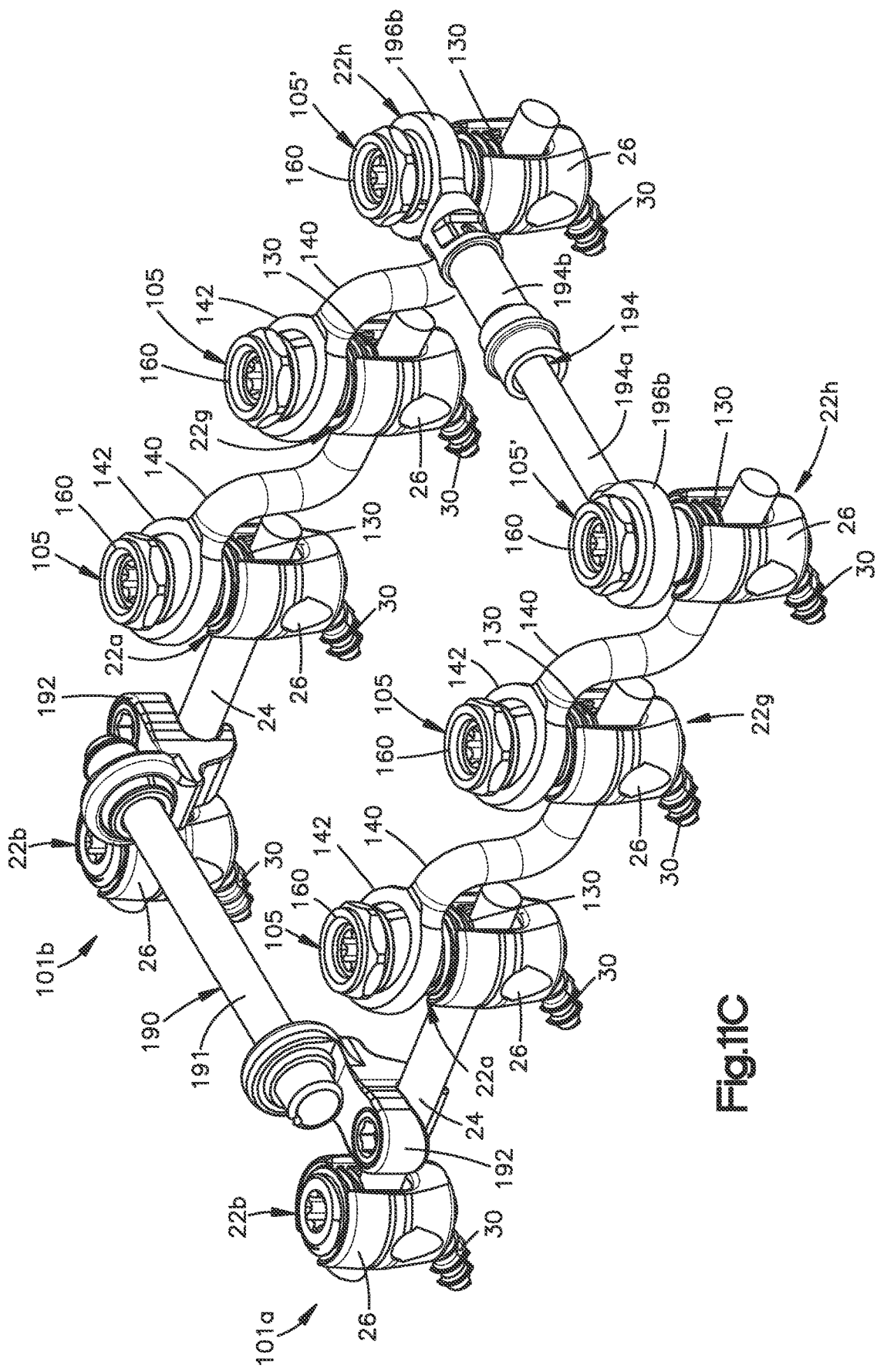
FIG. 11C is a perspective view of parallel rows of fixation elements connected by a cross bar.

Referring to FIGS. 11A-C, while the system 100 has been described for extending an existing construct to one adjacent spinal level, such as superior vertebrae 27g or inferior vertebra 27e as illustrated, the system 100 can further include two or more top-loading polyaxial cascading construct extenders 105 and a corresponding number of newly implantable bone fixation elements 22, such that the system can be used to attach multiple vertebrae that were previously not fixed. For instance, the polyaxial construct extender 105 can be attached to the newly implanted bone fixation element 22g in the manner described above, and a newly implanted bone fixation element 22 can be attached to an adjacent superior vertebral body 27h in the manner described above with respect to the vertebral body 27g. An extender rod 140 can then be connected between the polyaxial construct extender 105 attached to the bone fixation element 22g and the newly implanted bone fixation element 22 that was implanted in the vertebral body 27h. It should thus be appreciated that the cascading construct extenders 105 can be fixed to newly implanted vertebral bodies 27g and 27h without being fixed to a previously implanted fixation system.

The implantation of the cascading construct extenders can be minimally invasive, as a single incision can be made that accommodates a cannulated tube at a single vertebral level, as opposed to creating an incision along all vertebral levels to be fixed. The implantation can be performed at each vertebral level through a cannulated tube or retractor that extends through the incision, and the tube can be pivoted or the retractor can be pivoted or expanded so as to provide access to the adjacent vertebral levels to be implanted with the cascading construct extender 105.

It should be appreciated, as illustrated in FIG. 11A, that the cascading extender system 100 can be include only top loading polyaxial construct extenders 105 alone or in combination with a corresponding plurality of previously implanted bone fixation elements 22. The plurality of individual extender rods 140 substitute for the spine fixation rod 24 and the polyaxial bushings 150 retained within the loops 142 as desired so as to provide the desired angular adjustment capabilities and allow for top loading connections to the anchor seats 26 of the newly implantable bone fixation elements 22.

The conventional cervical spine surgical art typically utilizes hooks that generally require a first shallow trajectory to anchor the hook into bone and then a second, vertical trajectory to couple the hook to a spinal rod 120. The two disparate trajectories may necessitate a large incision for accessing the surgical site. The operational method for using the system 100 illustrated in FIG. 11A generally requires only one trajectory to implant each newly implantable bone fixation element 22 and top loading polyaxial construct extender 105, introduce the extender rod 140, and finally tighten the locking nut 160. Accordingly, the system 100 of the third preferred embodiment permits percutaneous stab incisions or one small incision to be utilized instead of a large incision. The trajectory for use during the implantation of the system 100 may be similar to the widely used Magerl technique and trajectory.

As illustrated in FIGS. 12A-B, the system 100 can further include one or both cross connectors 190 and 193 that are configured to join the rows 101a and 101b. The cross connector 190 includes a transverse connector rod 191 and a clamp 192 connected to the opposing ends of the rod 191 that are each configured to receive and secure to the spine fixation rod 24 of the rows 101a and 101b. The cross connector 193 includes a transverse connector rod 194 that defines a pair of rod segments 194a and 194b that can be joined together using any suitable mechanical joint 195. The transverse connector rod 194 includes a first loop 196a disposed at the outer end of the first rod segment 194a, and a second loop 196b disposed at the opposed outer end of the second rod segment 194b. Each loop 196a-b can be constructed as described above with respect to the loop 142 of the extender rod 140. Thus, the system 100 can include a spinal construct extender 105' modified with respect to the spinal construct extender 105 in that the cross connector 193 replaces the extender rod 140. The modified spinal construct extender 105' can be attached to the outermost bone fixation elements 22 in the manner described above, such that the transverse connector rod 194 is connected between the outermost vertebral implants 75 of the rows 101a and 101b.

Referring now to FIG. 13, it should be appreciated that the top-loading polyaxial construct extender 105 can be constructed in accordance with an alternative embodiment. In particular, the extender 105 can be constructed as described above, however the extension member 139 is constructed as a plate 180 having a plate body 181 that defines a proximal end 181a, a distal end 181b that is opposite the proximal end 181a along a central longitudinal axis 185, and a middle portion 181c disposed between the proximal end 181a and the distal end 181b. The distal end 181b can be pivotally movable about arrow 187 with respect to the middle portion 181c so as to conform to the anatomical topography of the underlying bone to be fastened. The plate body 180 includes an engagement member illustrated as a loop 182 that is connected to the proximal end 181a. The loop 182 is constructed as described above with respect to the loop 142 of the rod 140, such that the bushing 150 is retained within the loop 182 in the manner described above.

The plate 180 defines a plurality of apertures 183 that extend through the middle portion 181c and the distal end 181b, and are thus longitudinally spaced along the length of the plate body 181. The apertures 183 are each configured to receive a bone fastener, such as the bone fastener 30 described above, which can be compressive screws or locking screws, so as to secure the plate body 181 directly to an underlying bone, such as a vertebral body 27 or a lamina. The apertures 183 can include at least one circular aperture 184 sized to receive the bone fastener in a fixed position, and at least one longitudinally elongate aperture or slot 186 sized to receive the bone fastener such that the bone fastener is translatable within the slot 186 so as to assist with alignment of the bone fastener and the underlying bone prior to securing the bone fastener against the plate body 181. Alternatively, the slot 186 can retain bone graft material that is inserted into the plate body 181 during a laminoplasty procedure. In accordance with the illustrated embodiment, the extension plate 180 is malleable to allow some preoperative or intraoperative adjustment of the plate body geometry. One or more, up to all of the apertures 183 can be unthreaded so that the anchor 30 can compress the plate against the underlying bone, or one or more up to all of the apertures 183 can be threaded so that the bone anchor 30 can present complementary threads that mate with the threads of the apertures 183 so as to fix, or lock, the plate 180 to underlying bone without compressing the bone against the underlying bone.

During operation, the extender 105 is coupled to a previously implanted or newly implanted or newly implantable polyaxial bone fixation element 22 in the manner described above. The second end of the extension plate 180 can be anchored to bone directly, such as the lamina arch of a vertebral body. The top loading polyaxial plate extender 105 including the extension plate 180 is generally configured to contain graft, especially with open door laminoplasty procedures (such that the underlying bone is allograft) and/or with longer cervical-occipital fusion constructs. For instance, the plate 180 can be placed over the vertebral bodies 27 to be fixed, and the bone anchors 30 of the bone fixation elements 22 can be inserted through the complementary apertures 183 so as to fix both the fixation elements 22 and the plate 180 to the underlying vertebrae 27. Thus, the plate provides the ability to combine a laminoplasty procedure with a posterior fusion procedure using a single construct. Conventional constructs typically utilize cabling to contain such grafts, and the extension plate 180 provides a generally more rigid method of graft containment, and the top loading polyaxial coupling capabilities provided by the extender 105 provides a rigid fixation point when anatomical structures are not available or adequate to serve as an attachment point. Furthermore, the top loading attachment point is typically faster and easier to assemble than the current wiring technology.

Referring now to FIGS. 10A-D and 13, the extender 105 can include an extension member 139 in the form of a rod 206 that defines a proximal end 206a and a distal end 206b opposite the proximal end along a central rod axis 210, and a middle portion 206c disposed between the proximal end 206a ad the distal end 206b. The rod 206 includes an engagement member illustrated as a loop 207 that is connected to the proximal end 206a. The rod 206 further includes a bushing 150 that is retained in the loop 207 in the manner described above with respect to the loop 142. The middle portion 206c and the distal end 206b can be angularly offset with respect to the loop 207 as desired. In this regard, a kit of rods 206 can include define different angles between the middle portion 206c and/or distal end 206b and the loop 207.

During operation, the extender 105 can connect a previously implanted or newly implantable bone fixation element 22 to a previously-implanted translaminar screw. In particular, the locking cap 34 is removed, and the tapered set screw 130 is coupled to the previously implanted bone fixation element 22 in the manner described above. The rod 206 is then connected between the bone fixation element 22 and the translaminar screw by placing the bushing 150 around the middle portion 130c of the tapered set screw 130 and the distal end 206b into the rod seat of the translaminar screw. The translaminar screw can be constructed as described above with respect to the vertebral implant 75, and is used to fix adjacent vertebrae and fuse them together as known in the art. In particular, the translaminar screw is inserted through the facets and laminae of adjacent vertebrae in order to fix the adjacent vertebrae together.

The locking nut 160 is then screwed down over the superior or proximal portion 130*a* of the tapered set screw 130, thereby forcing the extender rod 206 and the bushing 150 to advance distally with respect to the middle portion 130*c* of the tapered set screw 130 and, in so doing, forcing the bushing 150 to expand and match tapers of the interior of the bushing 150 and the exterior of the middle portion of the tapered set screw 130 to lock via an interference fit, as described above. The locking cap 34 of the translaminar screw is then screwed into the top of the anchor seat of the translaminar screw until the angular orientation of the bone anchor 30 of the translaminar screw is locked with respect to the anchor seat 26 of the translaminar screw so as to lock the extender rod 206 in to the translaminar screw assembly.

It should be appreciated that the extender 105 can connect at a first end (including the polyaxial loop 207 and bushing 150) to the translaminar screw and can be rotate about the rod axis 210 along the direction of Arrow 211 as well as about the central screw axis B along the direction or Arrow 213, thereby providing an additional degree of freedom with respect to a plate that does not provide polyaxial rotation.

Referring now to FIGS. 9-10D and 14A-B, the fixation system 100 can be configured to connect a bone fixation element 22 of a bone fixation assembly 20 that is implanted in the cervical region of the spine to an occipital plate 250 that is configured to be fastened to the occiput 253. The occipital plate 250 may assume a variety of forms known in the art, and can include a central body 257 that includes an engagement member 252 configured to receive the distal end 141*b* of the extender rod 140. For instance, the engagement member 252 can include an aperture extending longitudinally through the central body 257 that is sized to receive the distal end 141*b* of the extender rod 140, and a set screw configured to lock against the extender rod 140. A pair of occipital plates 250 is illustrated as fastened to the distal end 141*b* of each extender rod 140, each having respective plate sections 250*a* and 250*b* that project outward and opposite each other from the engagement member 252. Each plate section 250*a* and 250*b* can be independently rotatable about the rod 140 or rotatably in unison about the rod 140. Additionally or alternatively, each plate section 250*a* and 250*b* can flex about the central body 257. Each plate section 250*a* and 250*b* can include at least one bone fixation aperture 255 extending therethrough that is sized to receive a bone fastener 30, such as a screw or a hook, so as to secure the plate sections 250*a* and 250*b* to an underlying bone, such as the occiput.

During operation, a fixation assembly 20 is pre-implanted in the cervical region of the spine, such that the bone fixation elements 22 can be implanted in respective underlying cervical vertebrae. The extender 105 is attached to the cranial most bone fixation element 22, which can be newly implanted or implantable, or previously implanted into a cervical vertebra C, after the locking cap 34 has been removed in the manner described above (e.g., to the vertebral implant 75 of the cranial most bone fixation element 22). The second, rod-shaped distal end 141*b* of the extender rod 140 is coupled to the occipital plate 250 using any of a variety of attachment mechanisms known in the art. In accordance with the illustrated embodiment, the system 100 can include first and second columns 101*a* and 101*b* of fixation elements 22 and spinal construct extenders 105 that couple the cranial most fixation element to an adjacent bone, which is illustrated as the occiput.

The top-loading polyaxial construct extender 105 enables the surgeon to have hinged capability when connecting the occiput to the cervical spine to enhance surgical ease and flexibility. The extender rod 140 can be prebent at a desired angle with respect to the loop 142, and is shorter in length than the conventional hinged rods used for such applications. Accordingly, the top-loading polyaxial construct extender 105 is easier to handle and connect between the cervical spine and the occiput. Further, the use of the top-loading polyaxial construct extender 105 allows a surgeon to build a cervical spinal construct and then decide if it is desired to add occipital fusion hardware, whereas, conventional hinged rods cause one to commit to instrumentation and hardware at the beginning of surgery.

It should be appreciated that a plurality of revision connector embodiments has been described herein. Thus a spine fixation revision connector kit can be provided that includes a plurality of revision connectors, each revision connector being configured to couple at least one vertebral body to an adjacent bone, which can be another vertebral body for example or can be the occiput. At least one revision connector a plurality of revision connectors in a revision connector kit defines a difference with respect to at least another of the plurality of revision connectors in the kit. For instance, the different revision connector can have a different length or construction of the polyaxial extension member 139. Alternatively or additionally, the screw 130 of the different revision connector can be straight instead of tapered, such that the set screw 130 does not lock the bushing 150 in the respective loop, thereby allowing the bushing to articulate in the respective loop after fixation. Alternatively stated, the loop 142, and thus the polyaxial extension member 139, can pivot or articulate in the locked position relative to the screw 130 and vertebral implant 75 to which the screw is fastened. Alternatively or additionally still, the distal portion 130*b* of the screw 130 can include a borehole or a full throughhole that includes a distally disposed interior set of threading that is configured to engage a set of threading on the exterior of the anchor seat 26 of the previously implanted or newly implantable vertebral implant 75 so as to accommodate the variety of vertebral implants or hooks that includes exterior threading configured for use with interiorly threaded set screws or locking caps.

It will be appreciated by those skilled in the art that changes could be made to the embodiments described above without departing from the broad inventive concept thereof. It is understood, therefore, that this invention is not limited to the particular embodiment disclosed, but it is intended to cover modifications within the spirit and scope of the present invention as defined by the present description.

We claim:

1. A method of extending a spinal construct, the method comprising:
    coupling a first portion of an extension member to a bone fixation element that is coupled to a first vertebra, the bone fixation element coupled to a spine fixation rod;
    coupling a second portion of the extension member to a second bone fixation element;
    securing the second bone fixation element to a second vertebra; and
    flexing the extension member from a first configuration to a second configuration, wherein the extension member is configured such that the second portion is movable with respect to the first portion.

2. The method of claim 1, wherein coupling the second portion of the extension member includes coupling the second portion such that the second vertebra is movable relative to the first vertebra.

3. The method of claim 1, wherein the flexing step is performed after the coupling the second portion of the extension member step.

4. The method of claim 1, wherein the extension member comprises a flexible polymeric material.

5. The method of claim 1, wherein coupling the second portion of the extension member to the second bone fixation element includes coupling the second portion of the extension member to the second bone fixation element such that the second bone fixation element is disposed within an aperture that extends through the extension member.

6. The method of claim 1, wherein the extension member includes a rod and an engagement member having an interior surface that defines an aperture and extends from a proximal end of the rod, and
wherein the method includes inserting a bushing into the aperture, the bushing having a bushing interior surface that defines a hollow interior to receive the second bone fixation element.

7. The method of claim 6, further comprising pressing an exterior surface of the bushing against the interior surface of the engagement member to fix a position of the bushing relative to the bone fixation element.

8. The method of claim 6, wherein at least one of a middle portion of the second bone fixation element and the bushing interior surface is tapered, and
wherein the method includes expanding the bushing against the engagement member when the second bone fixation element is inserted through the aperture of the engagement member.

9. The method of claim 6, wherein the bushing has a partially spherical external surface, the interior surface of the engagement member is partially spherical, and the method includes polyaxially pivoting the extension member with respect to the bushing.

10. The method of claim 6, wherein the bushing is inserted into the aperture of the engagement member before coupling the second portion of the extension member to the second bone fixation element.

11. The method of claim 6, wherein the extension member and the engagement member are integral with one another such that the extension member and the engagement member engage the second bone fixation element simultaneously.

12. The method of claim 6, wherein the method includes directly engaging the second bone fixation element with the bushing interior surface to thereby couple the extension member to the bone fixation element.

13. The method of claim 1, wherein the spinal construct includes the spine fixation rod fixed to the bone fixation element with a locking cap that fastens the spine fixation rod to the bone fixation element, and
wherein the method includes replacing the locking cap with a fastener configured to engage the extension member.

14. A method of extending a spinal construct, the method comprising:
coupling a first portion of an extension member to a bone fixation element that is coupled to a first vertebra, the bone fixation element coupled to a spine fixation rod;
coupling a second portion of the extension member to a second bone fixation element;
securing the second bone fixation element to a second vertebra; and
polyaxially pivoting the extension member with respect to the second bone fixation element, wherein the extension member is configured such that the second portion is movable with respect to the first portion.

15. The method of claim 14, further comprising flexing the extension member from a first configuration to a second configuration.

16. The method of claim 1, further comprising coupling a locking member to the second bone fixation element to lock the extension member to the second bone fixation element.

17. The method of claim 1, wherein the spinal construct includes the bone fixation element that is coupled to the first vertebra, an anchor seat that receives the bone fixation element and a spine fixation rod, and a locking cap that fastens the spine fixation rod to the anchor seat, and
wherein the method includes removing the locking cap before coupling the first portion of the extension member to the second bone fixation element.

18. The method of claim 17, wherein method step includes threadedly coupling a fastener to the anchor seat, the fastener configured to engage the extension member.

19. A method of extending a spinal construct, the method comprising:
coupling a first portion of an extension member to a bone fixation element that is coupled to a first vertebra, the bone fixation element coupled to a spine fixation rod;
coupling a second portion of the extension member to a second bone fixation element; and
securing the second bone fixation element to a second vertebra,
wherein the extension member is configured such that the second portion is movable with respect to the first portion,
wherein the extension member includes an extension member body that defines a proximal end and an opposed distal end that is spaced from the proximal end along a first direction, the body being bent at a location between the distal end and the proximal end such that an entirety of the distal end is lower than the proximal end along a second direction that is perpendicular to the first direction, the extension member further including an engagement member coupled to the proximal end, and
wherein coupling the second portion of the extension member to the second bone fixation element includes aligning the extension member such that the extension member body is vertically offset along the second direction with respect to the engagement member.

20. The method of claim 19, further comprising flexing the extension member from a first configuration to a second configuration.

* * * * *